US011826356B2

(12) United States Patent
Zhao

(10) Patent No.: US 11,826,356 B2
(45) Date of Patent: Nov. 28, 2023

(54) METHODS AND COMPOSITIONS FOR IMPROVING BONE MARROW HEMATOPOIETIC FUNCTIONS

(71) Applicant: Sun Yat-Sen University, Guangdong (CN)

(72) Inventor: Meng Zhao, Guangdong (CN)

(73) Assignee: Sun Yat-Sen University, Guangzhou (CN)

(*) Notice: Subject to any disclaimer, the term of this patent is extended or adjusted under 35 U.S.C. 154(b) by 453 days.

(21) Appl. No.: 16/606,495

(22) Filed: Oct. 18, 2019

(65) Prior Publication Data

US 2021/0369691 A1 Dec. 2, 2021

Related U.S. Application Data

(63) Continuation-in-part of application No. PCT/CN2019/085350, filed on Apr. 30, 2019.

(30) Foreign Application Priority Data

May 2, 2018 (CN) ......................... 201810411330.8
Oct. 21, 2018 (CN) ......................... 201811225757.5

(51) Int. Cl.
*A61K 31/4409* (2006.01)
*A61P 7/00* (2006.01)

(52) U.S. Cl.
CPC ............ *A61K 31/4409* (2013.01); *A61P 7/00* (2018.01)

(58) Field of Classification Search
CPC .............................. A61K 31/4409; A61P 7/00
See application file for complete search history.

(56) References Cited

U.S. PATENT DOCUMENTS

2006/0270631 A1* 11/2006 Smith .................. A61K 31/685 514/78

FOREIGN PATENT DOCUMENTS

CN 108670969 10/2018

OTHER PUBLICATIONS

Adamiak et al., 8(39) Oncotarget 65588-65600 (2017) (Year: 2017).*
Translation of CN Second Office Action, Application No. or Publication No. 201810411330.8, dated Feb. 7, 2020, (4 pages).
Mateusz Adamiak, et al., Mobilization studies in mice deficient in sphingosine kinase 2 support a crucial role of the plasma level of sphingosine-1-phosphate in the egress of hematopoietic stem progenitor cells, Jul. 24, 2017 (13 pages).
Translation of CN Office Action, Application No. or Publication No. 201810411330.8, (6 pages).
Patent Abstract for CN108670969m date of publication Oct. 19, 2018, (1 page).
Zhiqiang Qin et al., Targeting sphingosine kinase induces apoptosis and tumor regression for KSHV-associated primary effusion lymphoma, Mol. Cancer Ther. Jan. 2014; 13(1) pp. 154-164, (19, pages).

* cited by examiner

*Primary Examiner* — Timothy R Rozof
(74) *Attorney, Agent, or Firm* — Gunther Evanina; BUTZEL LONG

(57) ABSTRACT

The present application provides methods and compositions for treating diseases related to hematopoietic dysfunction and/or injury, by attenuating the expression and/or function of SphK2.

3 Claims, 16 Drawing Sheets

METHODS AND COMPOSITIONS FOR IMPROVING BONE MARROW HEMATOPOIETIC FUNCTIONS

CROSS-REFERENCE TO RELATED APPLICATIONS

The present application is a continuation-in-part application based on International Patent Application No. PCT/CN2019/085350, filed on Apr. 30, 2019, which claims priority to the Chinese Patent Application No. 201810411330.8 filed on May 2, 2018 and to the Chinese Patent Application No. 201811225757.5 filed on Oct. 21, 2018, respectively, each of which is incorporated herein by reference in their entirety.

FIELD OF THE INVENTION

The present application relates to methods and compositions for recovering and/or increasing hematopoietic system functions, such as use of a SphK2 inhibitor for treating diseases of a primary hematopoiesis dysfunction, a hematopoietic injury caused by radiation (e.g., radiotherapy) or chemotherapy, and for promoting functional recovery of hematopoietic and immune systems in a patient subjected to bone marrow transplantation.

BACKGROUND

Hematopoietic stem cells are a group of primitive hematopoietic cells existing in hematopoietic tissues, and mainly serve to differentiate to produce various blood cells, such as red blood cells, platelets and white blood cells, to support the renewal of hematopoietic and immune systems of the body. Hematopoietic stem cells play an important role in the maintenance and post-injury repair of normal hematopoietic function of the body. Primary lesions, radiation from the environment, and chemical drugs and radiation in clinical treatment can all cause serious injuries to hematopoietic stem and progenitor cells, resulting in hematopoiesis dysfunction, poor hemogram index, white blood cell decrease, immune dysfunction, and even survival rate reduction in the patients. Therefore, to expand hematopoietic stem cell number and/or improve the hematopoietic function of hematopoietic stem cells is crucial to the treatment of hematopoiesis dysfunction and related diseases. Improving the hematopoietic stem cell number and function is also critical for accelerating hematopoiesis reconstitution for patient subjected to bone marrow transplantation.

However, currently, there is very limited therapeutic interventions that are effective in expanding hematopoietic stem cell number and/or improving their functions.

SUMMARY

The present application relates to methods, systems and compositions for preventing, treating and/or alleviating hematopoietic dysfunction, hematopoietic injury, hematopoietic stem cell injury, poor hemogram index or immune cell reduction, for expanding hematopoietic stem cell number, for improving the hematopoietic function of hematopoietic stem cells, and/or for promoting hematopoietic recovery after bone marrow transplantation, by attenuating the expression and/or activity of SphK2, e.g., with an SphK2 inhibitor. The present application also relates to methods and systems for screening candidate agents for treating diseases related to hematopoietic dysfunction and/or hematopoietic stem cell injury, based on an effect of such candidate agents in attenuating the expression and/or activity of SphK2.

In one aspect, the present application provides use of a SphK2 inhibitor in the preparation of a medicament for treating a disease of hematopoietic dysfunction, a hematopoietic stem cell injury, poor hemogram index or immune cell reduction, improving self-renewal and hematopoietic function of hematopoietic stem cells, or promoting recovery after bone marrow transplantation.

In some embodiments, the present application provides use of a SphK2 inhibitor in the preparation of a medicament for improving poor hemogram index or immune cell reduction, for treating a disease of hematopoietic dysfunction caused by hematopoietic stem cell and/or progenitor cell injury, for improving self-renewal and hematopoietic function of hematopoietic stem cells or promoting recovery after bone marrow transplantation.

The present disclosure provides use of a SphK2 inhibitor in the preparation of a medicine for treating a disease related to hematopoietic dysfunction, a hematopoietic or hematopoietic stem cell injury, poor hemogram index or immune cell reduction, expanding hematopoietic stem cell number and improving hematopoietic function of hematopoietic stem cells, or promoting hematopoietic recovery after bone marrow transplantation.

In another aspect, the present application provides a SphK2 inhibitor, used for treating a disease of hematopoietic dysfunction, a hematopoietic or a hematopoietic stem cell injury, poor hemogram index or immune cell reduction, improving self-renewal and hematopoietic function of hematopoietic stem cells, or promoting recovery after bone marrow transplantation.

In some embodiments, the present application provides a SphK2 inhibitor, for the use of treating a disease related to hematopoietic dysfunction, a hematopoietic injury, poor hemogram index or immune cell reduction, the use of expanding hematopoietic stem cell number and improving hematopoietic function of hematopoietic stem cells, or the use of promoting hematopoietic recovery after bone marrow transplantation.

In a further aspect, the present application provides a method for treating a disease related to hematopoietic dysfunction, a hematopoietic stem cell injury, poor hemogram index or immune cell reduction, improving self-renewal and hematopoietic function of hematopoietic stem cells, or promoting recovery after bone marrow transplantation, comprising administering a SphK2 inhibitor and a pharmaceutically acceptable carrier to a subject in need thereof.

In some embodiments, the present application provides a method for treating a disease related to hematopoietic dysfunction, a hematopoietic injury, poor hemogram index or immune cell reduction, for expanding hematopoietic stem cell number and improving hematopoietic function of hematopoietic stem cells, or for promoting hematopoietic recovery after bone marrow transplantation, the method comprising administering to a subject in need a SphK2 inhibitor and a pharmaceutically acceptable carrier.

In one or more embodiments, the disease is primary or is caused by radiation or drug-induced injuries.

In one or more embodiments, the disease is primary hematopoietic dysfunction, a disease caused by environmental radiation, radiation in radiotherapy and/or chemotherapeutic drug-induced injuries, or a disease related to reduction of white blood cells and/or platelets.

In one or more embodiments, the SphK2 inhibitor promotes post-injury repair in white blood cells and platelets, and/or promotes recovery of the number of white blood cells and platelets after bone marrow transplantation.

In one or more embodiments, the SphK2 inhibitor inhibits the expression of a SphK2 gene or inhibits the function of a SphK2 protein.

In one or more embodiments, the hemogram comprises white blood cells and/or platelets.

In one or more embodiments, the medicament of the present application promotes post-injury repair in white blood cells and platelets, and/or promotes recovery of the number of white blood cells and platelets after bone marrow transplantation.

In one or more embodiments, the SphK2 inhibitor is ABC294640 having a molecular formula as follows:

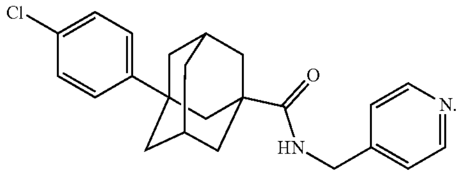

In one or more embodiments, the promoting recovery (such as hematopoietic recovery) after bone marrow transplantation comprises treating hematopoietic dysfunction after bone marrow transplantation.

In one or more embodiments, the promoting recovery (such as hematopoietic recovery) after bone marrow transplantation comprises improving self-renewal and hematopoietic function of hematopoietic stem cells.

In one or more embodiments, the promoting recovery (such as hematopoietic recovery) after bone marrow transplantation comprises expanding hematopoietic stem cell number and improving hematopoietic function of hematopoietic stem cells.

In one or more embodiments, the SphK2 inhibitor is used for treating hematopoietic dysfunction caused by primary hematopoietic stem cell function defect, for expanding hematopoietic stem cell number, for enhancing the function of hematopoietic stem cells, and/or for increasing the number of white blood cells and the number of platelets.

In one or more embodiments, the SphK2 inhibitor is used for treating hematopoietic dysfunction caused by radiation (such as radiation from the environment), for expanding hematopoietic stem cell number, for enhancing the function of hematopoietic stem cells, and/or for increasing the number of white blood cells and the number of platelets.

In one or more embodiments, the SphK2 inhibitor is used for treating hematopoietic dysfunction caused by radiotherapy, for expanding hematopoietic stem cell number, for enhancing the function of hematopoietic stem cells, and/or for increasing the number of white blood cells and the number of platelets.

In one or more embodiments, the SphK2 inhibitor is used for treating hematopoietic dysfunction caused by chemotherapy, for expanding hematopoietic stem cell number, for enhancing the function of hematopoietic stem cells, and/or for increasing the number of white blood cells and the number of platelets.

In one or more embodiments, the medicament for promoting recovery after bone marrow transplantation is used for treating hematopoietic dysfunction after bone marrow transplantation.

In one or more embodiments, the medicament for promoting recovery after bone marrow transplantation is used for expanding hematopoietic stem cell number, for enhancing the function of hematopoietic stem cells, for improving hematopoietic function of hematopoietic stem cells, and/or for promoting the recovery of white blood cells and platelets.

In one or more embodiments, the medicament for promoting recovery after bone marrow transplantation is used for enhancing the ability of hematopoietic stem cells to differentiate after bone marrow transplantation, such as to generate more donor derived blood cells after bone marrow transplantation.

In one or more embodiments, the medicament for promoting recovery (such as hematopoietic recovery) after bone marrow transplantation is used for increasing the number of platelets.

In one or more embodiments, the medicament for promoting recovery (such as hematopoietic recovery) after bone marrow transplantation is used for increasing the number of blood immune cells.

In another aspect, the present application provides use of a SphK2 gene or protein as a drug screening target, wherein the drug is a drug for treating a hematopoietic dysfunction (e.g., hematopoietic primary dysfunction) or injury, and/or hematopoietic stem cell injury.

In a further aspect, the present application provides a method for screening a drug for treating a hematopoietic injury and/or or diseases related to hematopoietic dysfunction, using a SphK2 gene or protein as a target, comprising:

(1) allowing a candidate agent to contact with an organism expressing the SphK2 gene or protein in vivo or in vitro;

(2) determining the expression or function of the SphK2 gene or protein before and after the contact; and (3) selecting a candidate agent that results in reduction of the expression or function of the SphK2 gene or protein, wherein the organism is a cell, a tissue or a mammal.

In one or more embodiments, the screening is performed in vivo or in vitro.

In one or more embodiments, the step of allowing a candidate agent to contact with an organism expressing the SphK2 gene or protein in vivo or in vitro is performed in vivo or in vitro.

In one or more embodiments, the drug is a drug for treating blood and immune system injuries.

In one or more embodiments, the drug is a drug for treating hematopoietic dysfunction and poor hemogram index.

In one or more embodiments, the hematopoietic injury, the hematopoietic stem cell injury, the hematopoietic dysfunction or poor hemogram index is primary, or caused by radiation or drug-induced injuries.

In one or more embodiments, the hematopoietic injury, the hematopoietic stem cell injury, the hematopoietic dysfunction or poor hemogram index is in patients subjected to bone marrow transplantation.

In one or more embodiments, the drug inhibits the expression of the SphK2 gene or the function of the SphK2 protein.

The present application provides use of a SphK2 gene or protein as a drug screening target, the drug being a drug for treating a hematopoietic injury.

In the use of a SphK2 gene or protein as a drug screening target, the drug is a drug for treating blood and immune system injuries.

In the use of a SphK2 gene or protein as a drug screening target, the drug is a drug for treating hematopoietic dysfunction and poor hemogram index.

In one or more embodiments, the hematopoietic injury, hematopoietic dysfunction and poor hemogram index are primary, or caused by radiation or drug-induced injuries. The drug inhibits the expression of the SphK2 gene or the function of the SphK2 protein.

In one aspect, the present application provides use of a SphK2 inhibitor in the preparation of a medicament for treating a disease of hematopoietic dysfunction, a hematopoietic injury, poor hemogram index or immune cell reduction, the disease being primary or caused by radiation or drug-induced injuries.

In another aspect, the present application provides use of a SphK2 inhibitor in the preparation of a medicament for expanding hematopoietic stem cell number, for improving hematopoietic stem cell self-renewal, and/or for improving hematopoietic function of hematopoietic stem cells. The SphK2 inhibitor inhibits the expression of a SphK2 gene or inhibits the function of a SphK2 protein. For example, the SphK2 inhibitor may be ABC294640.

In a further aspect, the present application provides use of a SphK2 inhibitor in the treatment of hematopoietic dysfunction after hematopoietic stem cell bone marrow transplantation, the disease being caused by bone marrow transplantation. The SphK2 inhibitor inhibits the expression of a SphK2 gene or inhibits the function of a SphK2 protein. For example, the SphK2 inhibitor may be ABC294640.

In one or more embodiments, the immune cells include white blood cells.

In one aspect, the present application provides a method for preventing, treating and/or alleviating a disease or disorder related to hematopoietic dysfunction and/or hematopoietic injury in a subject in need thereof, the method comprises attenuating an expression and/or function of SphK2 in the subject.

In some embodiments, the method of the present application comprises attenuating an expression and/or function of SphK2 in a hematopoietic stem cell and/or hematopoietic progenitor cell (HSPC) in the subject. The HSPC may be a bone marrow derived HSPC.

In another aspect, the present application provides a method for preventing, treating and/or alleviating a disease or disorder related to hematopoietic dysfunction and/or hematopoietic injury in a subject in need thereof, the method comprises administering to the subject an HSPC, wherein an expression and/or function of SphK2 of the HSPC is attenuated.

In another aspect, the present application provides a method for preventing, treating and/or alleviating a disease or disorder related to hematopoietic dysfunction and/or hematopoietic injury in a subject in need thereof, the method comprises administering to the subject an HSPC, wherein the HSPC is derived from a donor with attenuated expression and/or functions of SphK2.

In another aspect, the present application provides a method for screening a candidate agent for preventing, treating and/or alleviating a disease or disorder related to hematopoietic dysfunction and/or hematopoietic injury, the method comprises determining an ability of the candidate agent in attenuating an expression and/or function of SphK2.

In some embodiments, the disease or disorder related to hematopoietic dysfunction and/or hematopoietic injury comprises poor hemogram index, reduction of immune cells, reduction of white blood cells, reduction of platelets, and/or a bone marrow failure syndrome.

In some embodiments, the disease or disorder is primary.

In some embodiments, the disease or disorder is related to and/or caused by radiation or a therapy-induced injury.

In some embodiments, the therapy-induced injury comprises a radiotherapy-induced injury and/or a chemotherapy-induced injury.

In some embodiments, the chemotherapy comprises 5-fluorouracil.

In another aspect, the present application provides a method for increasing hematopoietic cell expansion in a subject in need thereof, the method comprises attenuating an expression and/or function of SphK2 in the subject.

In some embodiments, the method of the present application comprises attenuating an expression and/or function of SphK2 in an HSPC in the subject. The HSPC may be or may comprise a bone marrow derived HSPC.

In another aspect, the present application provides a method for promoting hematopoietic recovery after bone marrow transplantation in a subject in need thereof, the method comprises attenuating an expression and/or function of SphK2 in the subject.

In some embodiments, the expression and/or function of SphK2 is attenuated in the subject after the bone marrow transplantation.

In some embodiments, the method comprises attenuating an expression and/or function of SphK2 in an HSPC in the subject (e.g., after said bone marrow transplantation). The HSPC may be or may comprise a bone marrow derived HSPC.

In another aspect, the present application provides a method for promoting hematopoietic recovery after bone marrow transplantation in a subject in need thereof, the method comprises attenuating an expression and/or function of SphK2 in a HSPC of the bone marrow being transplanted.

In another aspect, the present application provides a method for promoting hematopoietic recovery after bone marrow transplantation in a subject in need thereof, wherein the bone marrow is derived from a donor with attenuated expression and/or function of SphK2.

In another aspect, the present application provides a method for promoting hematopoietic recovery after bone marrow transplantation in a subject in need thereof, wherein the transplanted bone marrow comprises an HSPC with attenuated expression and/or function of SphK2.

In some embodiments, the hematopoietic recovery comprises a recovery of white blood cell number after the bone marrow transplantation, a recovery of platelet number after the bone marrow transplantation, a recovery from hematopoietic dysfunction after the bone marrow transplantation, an expansion of HSPC number after the bone marrow transplantation, an improvement of a hematopoietic function of an HSPC after the bone marrow transplantation, an enhancement of blood cell generation by an HSPC after the bone marrow transplantation, an increase of platelet number after the bone marrow transplantation, and/or an increase of blood immune cell number after the bone marrow transplantation.

In some embodiments, the subject according to any aspect of the present application has been subjected to chemotherapy.

In some embodiments, the chemotherapy comprises 5-fluorouracil.

In some embodiments, the subject according to any aspect of the present application has been subjected to radiation.

In some embodiments, the radiation comprises a radiotherapy.

In some embodiments, the subject according to any aspect of the present application has been subjected to bone marrow transplantation.

In some embodiments, the subject according to any aspect of the present application has a hematopoietic injury (such as an injury related to and/or caused by chemotherapy, radiation, e.g., radiotherapy, and/or a primary injury).

In another aspect, the present application provides a method for increasing HSPC number, the method comprises attenuating an expression and/or function of SphK2 of the HSPC.

In another aspect, the present application provides a method for expanding HSPC, the method comprises attenuating an expression and/or function of SphK2 of the HSPC.

In another aspect, the present application provides a method for promoting a self-renewal activity of an HSPC, the method comprises attenuating an expression and/or function of SphK2 of the HSPC.

In another aspect, the present application provides a method for increasing a regenerative potential of an HSPC, the method comprises attenuating an expression and/or function of SphK2 of the HSPC.

In another aspect, the present application provides a method for improving a hematopoietic function of an HSPC, the method comprises attenuating an expression and/or function of SphK2 of the HSPC.

In another aspect, the present application provides a method for maintaining and/or increasing quiescence of an HSPC, the method comprises attenuating an expression and/or function of SphK2 of the HSPC.

In some embodiments, the method of the present application is an in vitro method.

In some embodiments, the method of the present application is an in vivo method.

In some embodiments, the method of the present application is an ex vivo method.

In another aspect, the present application provides an HSPC obtained from a method according to the present application.

In another aspect, the present application provides an isolated HSPC, wherein an expression and/or function of SphK2 of the HSPC is attenuated.

In some embodiments, the HSPC has been modified to attenuate the expression and/or function of SphK2 of in the HSPC.

In another aspect, the present application provides a pharmaceutical composition, the composition comprises the HSPC according to the present application, and optionally a pharmaceutically acceptable carrier.

In some embodiments, according to any aspect of the present application, the expression and/or function of the SphK2 is attenuated by inhibiting an expression and/or function of the SphK2 gene, and/or inhibiting an expression and/or function of the SphK2 protein.

In some embodiments, according to any aspect of the present application, the expression and/or function of the SphK2 is attenuated with a SphK2 inhibitor.

In some embodiments, according to any aspect of the present application, the SphK2 inhibitor is a small molecule inhibitor.

In some embodiments, according to any aspect of the present application, the SphK2 inhibitor comprises a compound of formula (I) or a pharmaceutically salt thereof:

(I)

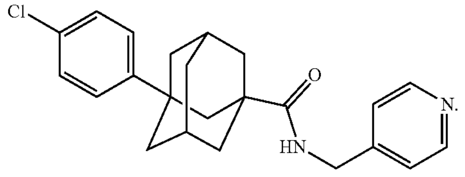 [SMILES: O=C(NCc1ccncc1)C12CC3CC(C1)CC(c1ccc(Cl)cc1)(C3)C2]

In some embodiments, according to any aspect of the present application, the SphK2 inhibitor comprises a compound of formula (II) or a pharmaceutically acceptable salt thereof:

(II)

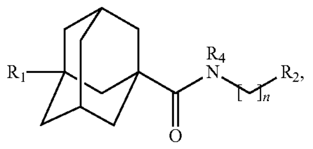

wherein:

$R_1$ is phenyl, or a phenyl substituted with a halogen; $R_2$ is aryl, heteroaryl, or a substituted aryl or heteroaryl; $R_4$ is H or alkyl; and n is an integer of at least 1.

In some embodiments, according to any aspect of the present application, the HSPC comprises a hematopoietic stem cell (HSC), a hematopoietic progenitor cell (HPC), a long-term HSC (LT-HSC), a short-term HSC (ST-HSC), a multipotent progenitor cell (MPP), and/or a CD150 HSC.

DETAILED DESCRIPTION

Figure 1:
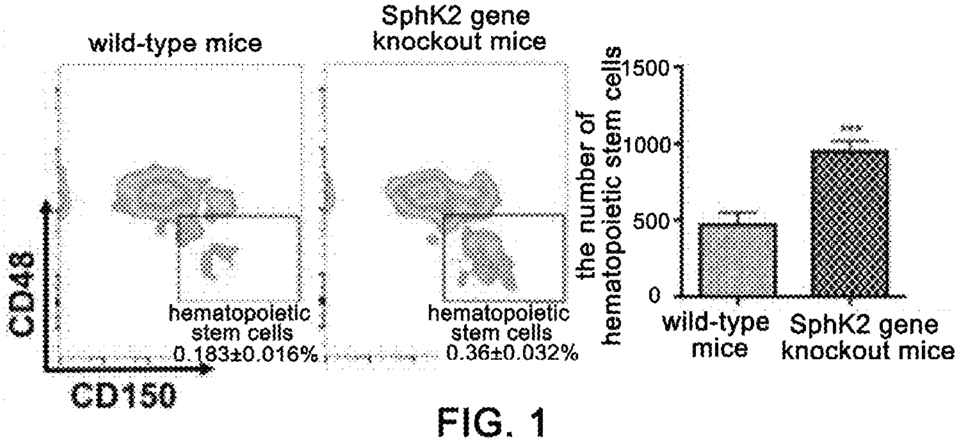
FIG. 1. SphK2 gene knockout led to an increase in the number of hematopoietic stem cells. Indicated in the box of the left graph was analysis of hematopoietic stem cells in the bone marrow cells of wild-type mice and SphK2 gene knockout mice, showing an increase in the proportion of hematopoietic stem cells after SphK2 gene knockout; and the right graph showed the calculated number of hematopoietic stem cells in bone marrow cells in the wild-type mice and in the SphK2 gene knockout mice. The results showed that the number of hematopoietic stem cells increased significantly in the SphK2 gene knockout mice.

In general, deletion of SphK2 gene (mouse NCBI accession number: NP_001166032, human Genbank Gene ID: 56848) is believed to result in slow growth, apoptosis and weakened tumor-forming ability in various tumor cells. By using SphK2 gene knockout mouse models, the present inventor first found that SphK2 gene knockout enhanced the self-renewal ability of hematopoietic stem cells and increased the number thereof, which was manifested in an increase of the number and function of hematopoietic stem cells in mice. It was also found in the present application that after the stimulation by radiation and chemotherapeutic drugs, the post-injury repair of hematopoietic system in SphK2 gene knockout mice was significantly accelerated, and the survival period of the mice was significantly prolonged under multiple chemotherapy stimulations, due to increased hematopoietic stem cell number and function. This suggests that SphK2 gene is an effective therapeutic target for targeting hematopoietic stem cells to treat hematopoietic dysfunction diseases.

It was also found by the present inventor that hematopoietic stem cells from SphK2 gene knockout mice gave accelerated hematopoietic reconstitution post-bone marrow transplantation, which was manifested in acceleration in the recovery of hematopoietic stem cell pool and platelets and blood immune cells after bone marrow transplantation. This indicates that SphK2 gene is an effective therapeutic target for targeting hematopoietic stem cells to treat hematopoietic dysfunction diseases after bone marrow transplantation.

ABC294640, also known as 3-(4-chloro-phenyl)-adamantane-1-carboxylic acid (pyridin-4-ylmethyl)-amide, has a structure as shown in formula (I). ABC294640 has been reported to be an inhibitor of sphingosine kinase 2 (SphK2) (see WO2006138660A2) and can reduce the production of sphingosine-1-phosphate (S1P). S1P is a second messenger of eukaryotic organisms, which can exert a variety of important physiological functions and can promote the growth of cancer tissues and the occurrence of pathological inflammations.

(I)

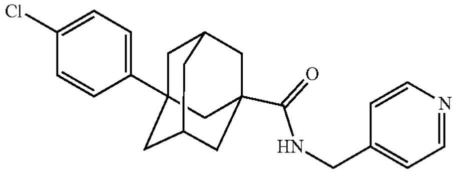

The present inventor has demonstrated for the first time use of SphK2 inhibitor ABC294640 for the treatment of hematopoietic dysfunction diseases. The inventor found that intraperitoneal injection of ABC294640 in mice could significantly increase the number and function of hematopoietic stem cells, showing a therapeutic effect on primary hematopoietic dysfunction. Moreover, ABC294640 could effectively promote the recovery of hematopoietic stem cell pool, platelets and white blood cells in mice after stimulation of the chemotherapeutic drug 5-fluorouracil and radiation-induced injury, and had remarkable improving effects on the hemogram, e.g., recovery of white blood cells and platelets, after being injured and stimulated; and the survival period of the mice injected with ABC294640 was significantly prolonged after multiple high-dose chemotherapy stimulations, indicating that ABC294640 has therapeutic effect on the decrease in survival rate caused by severe damages to the blood system.

The present application has also demonstrated for the first time use of SphK2 inhibitor (e.g., ABC294640) in the treatment of hematopoietic dysfunction diseases after bone marrow transplantation. The present inventor found that after hematopoietic stem cell bone marrow transplantation, SphK2 inhibitors (e.g. with intraperitoneal injection of ABC294640 in mice) could significantly increase the number of hematopoietic stem cells, and significantly accelerate the recovery of platelets and blood immune cells, and had remarkable improving effect on hemogram, e.g., the recovery of white blood cells and platelets, after hematopoietic stem cell bone marrow transplantation.

The present application has explored new medicinal value of SphK2 inhibitor (such as ABC294640, a small molecule compound), i.e., SphK2 inhibitors (such as ABC294640) are of therapeutic significance when used for treatment primary hematopoietic dysfunction, hematopoietic dysfunction caused by chemical drugs or radiation-induced injuries, and hemopoietic dysfunction after hematopoietic stem cell bone marrow transplantation.

The present inventor has demonstrated for the first time that SphK2 inhibitors (e.g., ABC294640, its functional derivatives and analogs) are effective in expanding hematopoietic stem cell number and promoting hematopoietic stem cell function for primary hematopoietic dysfunction diseases or post-injury repair of the blood system after environmental radiation, chemo- or radio-therapy and bone marrow transplantation.

The present application shows that the number of HSPCs (e.g., hematopoietic stem cells) increased significantly (e.g., among bone marrow cells) when the expression and/or functions of SphK2 is attenuated (e.g. as in SphK2 gene knockout mice).

The present application also shows that the number of HSPCs (e.g., hematopoietic stem cells) was significantly increased after chemotherapy-induced injury when the expression and/or functions of SphK2 is attenuated (e.g. as in SphK2 gene knockout mice). The use of a SphK2 inhibitor (e.g., ABC294640, its functional derivatives and analogs) resulted in a remarkable increase in the number of HSPCs (e.g., hematopoietic stem cells) after chemotherapy.

The present application also shows that a SphK2 inhibitor (e.g., ABC294640, its functional derivatives and analogs) remarkably promoted the post-injury repair of HSPCs (e.g., hematopoietic stem cells). The SphK2 inhibitor (e.g., ABC294640, its functional derivatives and analogs) significantly accelerated recovery of white blood cells after the stimulation of the chemotherapeutic drug (e.g. 5-fluorouracil). The SphK2 inhibitor (e.g., ABC294640, its functional derivatives and analogs) significantly accelerated recovery of platelets after the stimulation of the chemotherapeutic drug (e.g. 5-fluorouracil). The SphK2 inhibitor (e.g., ABC294640, its functional derivatives and analogs) significantly accelerated recovery of white blood cells after the stimulation of radiation. The SphK2 inhibitor (e.g., ABC294640, its functional derivatives and analogs) significantly accelerated recovery of platelets after the stimulation of radiation. The administration of a SphK2 inhibitor (e.g., ABC294640, its functional derivatives and analogs) after bone marrow transplantation resulted in a remarkable increase in the number of HSPCs (e.g., hematopoietic stem cells). The SphK2 inhibitor (e.g., ABC294640, its functional derivatives and analogs) significantly accelerated the recovery of white blood cells after bone marrow transplantation.

The present application also shows that a SphK2 inhibitor (e.g., ABC294640, its functional derivatives and analogs) significantly accelerated the recovery of platelets after bone marrow transplantation.

The present application shows that attenuating the expression and/or function of SphK2 (e.g., with SphK2 gene knockout) led to an enhancement of the function of HSPCs (e.g., hematopoietic stem cells). Sphk2 attenuated HSPCs (e.g., hematopoietic stem cells) provided significantly higher reconstitution. Sphk2 attenuated HSPCs (e.g., hematopoietic stem cells) were able to provide multi-hematopoietic lineage and more donor derived hematopoietic stem cells.

Further, SphK2 inhibitors (e.g., ABC294640, its functional derivatives and analogs) resulted in increased hematopoietic stem cell number and improved function.

Definitions

As used herein, the term "subject" generally refers to an individual. The subject may include, for example, domesticated animals, such as cats and dogs, livestock (e.g., cattle, horses, pigs, sheep, and goats), laboratory animals (e.g., mice, rabbits, rats, and guinea pigs), mammals, non-human mammals, primates, non-human primates, rodents, birds, reptiles, amphibians, fish, and any other animal. The subject may also comprise a mammal, such as a primate or a human.

As used herein, the term "alkyl" generally refers to a group and as a structural element of other groups, e.g., a substituted alkyl, it can be either straight-chained or branched. For example, alkyl includes methyl, ethyl, propyl, isopropyl, butyl, isobutyl.

As used herein, the term "aryl" generally refers to a monocyclic or fused bicyclic aromatic ring assembly containing six to ten ring carbon atoms. For example, aryl may be phenyl or naphthyl.

As used herein, the term "heteroaryl" generally refers to an aryl where one or more of the ring members are a heteroatom or moiety selected from —O—, —N=, —NR—, —C(O)—, —S—, —S(O)— or $—S(O)_2—$, wherein R may be a hydrogen, C1-C4 alkyl or a nitrogen protecting group.

As used herein, the term "cycloalkyl" generally refers to a saturated or partially unsaturated, monocyclic, fused bicyclic or bridged polycyclic ring assembly containing the number of ring atoms as indicated.

As used herein, the term "halogen" generally refers to chloro or fluoro, but may also be bromo or iodo.

As used herein, the term "hematopoietic stem cells" or "HSCs" generally refers to immature hematopoietic cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). HSCs are interchangeably described as stem cells throughout the specification. Such cells may include $CD34^+$ cells. $CD34^+$ cells are immature cells that express the CD34 cell surface marker. $CD34^+$ cells are believed to include a subpopulation of cells with the stem cell properties defined above. Such cells may include $CD150^+$ cells. $CD150^+$ cells are immature cells that express the CD150 cell surface marker. The $CD150^+$ cells may have long-term, multilineage-reconstituting ability. HSCs may also include pluripotent stem cells, multipotent stem cells (e.g., a lymphoid stem cell), and/or stem cells committed to specific hematopoietic lineages. The stem cells committed to specific hematopoietic lineages may be of T cell lineage, B cell lineage, dendritic cell lineage, Langerhans cell lineage and/or lymphoid tissue-specific macrophage cell lineage. In addition, HSCs may also include long term HSC (LT-HSC) and short term HSC (ST-HSC). ST-HSCs are more active and more proliferative than LT-HSCs. However, LT-HSC have unlimited self-renewal ability (i.e., they survive throughout adulthood), whereas ST-HSC have limited self-renewal ability (i.e., they survive for only a limited period of time). Any of these HSCs can be used in any of the methods described herein. Hematopoietic stem cells may be obtained from blood products. A blood product includes a product obtained from the body or an organ of the body containing cells of hematopoietic origin. Such sources include un-fractionated bone marrow, umbilical cord, peripheral blood, liver, thymus, lymph and spleen. All of the aforementioned crude or un-fractionated blood products can be enriched for cells having hematopoietic stem cell characteristics.

As used herein, the term "treating" or "treatment" generally refers to alleviating or abating a disease, a disorder and/or at least one of its attendant symptoms.

As used herein, the term "expansion" or "expanding" when used in connection with a cell or cells, generally refers to an increase in the number of a characteristic cell type, or cell types, from an initial cell population of cells, which may or may not be identical. The initial cells used for expansion may not be the same as the cells generated from expansion.

As used herein, the term "hematopoietic stem cell and/or progenitor cell" or "HSPC" generally refers to a hematopoietic stem cell and/or a hematopoietic progenitor cell. In some cases, the terms "HSPC" "HSC" may be used interchangeably. The HSPC of the present application may comprise a hematopoietic stem cell (HSC), a hematopoietic progenitor cell (HPC), a long-term HSC (LT-HSC), a short-term HSC (ST-HSC), a multipotent progenitor cell (MPP), and/or a $CD150^+$ HSC.

As used herein, the term "primary" when used in connection with a disease or disorder, generally refers to a disease or disorder arising spontaneously and not associated with or caused by a previous disease or injury.

As used herein, the term "enhancing hematopoietic recovery", "promoting hematopoietic recovery", or "increasing hematopoietic recovery" generally refers to an increase in the hematopoiesis detected in a subject caused by a treatment compared to the hematopoiesis in the subject before the treatment or in an otherwise identical but untreated subject.

As used herein, the term "quiescence" or "quiescent" when used in connection with an HSC, generally refers to the HSC being in a state of reversible growth arrest, for prolonged periods of time. It may represent a state of poised potential and active restraint.

As used herein, the term "isolated" when used in connection with a cell (such as an HSC), generally refers to a cell or cells that has been removed from an organism or population of cells in which it was originally found, or a descendant of such a cell. Optionally the cell has been cultured in vitro, e.g., in the presence of other cells and/or an appropriate culture medium.

As used herein, the term "small molecule" generally refers to a low molecular weight (e.g., lower than about 900 Dalton) compound (such as an organic compound).

Methods of Disease Prevention and/or Treatment

In one aspect, the present application provides methods for preventing, treating and/or alleviating a disease or disorder related to hematopoietic dysfunction and/or hematopoietic injury in a subject in need thereof.

In another aspect, the present application provides a method for increasing hematopoietic cell (e.g., HSPCs, or HSCs) expansion in a subject in need thereof.

The method may comprise attenuating an expression and/or function of SphK2 in the subject. For example, by attenuating an expression and/or function of the SphK2 in the bone marrow of the subject, e.g., in one or more HSPCs in the subject. The HSPC may be a bone marrow derived HSPC.

In some cases, the method may comprise administering to the subject an HSPC, wherein an expression and/or function of SphK2 of the HSPC is attenuated.

In some cases, the method may comprise administering to the subject one or more HSPCs derived from a donor with attenuated expression and/or functions of SphK2. For example, the expression and/or function of SphK2 of the donor may be attenuated, and then, one or more HSPCs may be obtained from such a donor, and provided/administered to the subject.

The subject may, for example, be a bone marrow donor or an individual with or at risk for depleted or limited blood cell levels. In some cases, the subject may be a bone marrow donor prior to bone marrow harvesting or a bone marrow donor after bone marrow harvesting.

In some cases, the subject may be a recipient of a bone marrow transplant. The subject may have limited bone marrow reserve such as elderly subjects or subjects previously exposed to an immune depleting treatment or myeloablative treatment such as chemotherapy, radiotherapy, and/or radiation from the environment.

The subject may have a decreased blood cell level or is at risk for developing a decreased blood cell level as compared to a control blood cell level. The control blood cell level may refer to an average level of blood cells in a subject prior to or in the substantial absence of an event that changes blood cell levels in the subject. An event that changes blood cell levels in a subject includes, for example, anemia, trauma, chemotherapy, bone marrow transplant, radiation therapy and/or radiation in the environment. For example, the subject may have anemia or blood loss due to, for example, trauma.

The subject may have depleted bone marrow related to, for example, congenital, genetic or acquired syndrome characterized by bone marrow loss, or depleted bone marrow. Thus, the subject may be a subject in need of hematopoiesis. For example, the subject may be a bone marrow donor or is a subject with or at risk for depleted bone marrow.

The expression and/or function of SphK2 may be attenuated, for example, before, at the same time, or after chemotherapy, radiation therapy or a bone marrow transplant.

The present application also provides a method for promoting hematopoietic recovery after bone marrow transplantation in a subject in need thereof.

The method may comprise attenuating an expression and/or function of SphK2 in the subject. The expression and/or function of SphK2 in the subject may be attenuated in the bone marrow. In some cases, the expression and/or function of SphK2 in the subject may be attenuated in the HSPCs in the subject.

For example, the expression and/or function of SphK2 in the subject may be attenuated after the bone marrow transplantation.

In some cases, the subject may be administered with one or more HSPCs with attenuated expression and/or function of SphK2. In some cases, the bone marrow that has been transplanted comprises one or more HSPCs with attenuated expression and/or function of SphK2.

In some cases, the bone marrow that has been transplanted may be derived from a donor that has attenuated expression and/or function of SphK2.

The hematopoietic recovery may comprise a recovery of white blood cell number, a recovery of platelet number, a recovery from hematopoietic dysfunction, an expansion of HSPC number, an improvement of a hematopoietic function of an HSPC, an enhancement of blood cell generation by an HSPC, an increase of platelet number, and/or an increase of blood immune cell number, e.g., after bone marrow transplantation.

The method of the present application may be used as a supplemental treatment to chemotherapy and/or radiation therapy. For example, the subject may be a subject that has been subjected to, is undergoing or is expected to undergo an immune cell depleting treatment such as chemotherapy, radiation therapy or serving as a donor for a bone marrow transplant. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy. Therefore, the methods of the present application may be applied to such subjects. In some cases, the subject has received bone marrow transplantation.

The disease or disorder may comprise poor hemogram index, reduction of immune cells, reduction of white blood cells, reduction of platelets, and/or a bone marrow failure syndrome. The disease or disorder may be primary, or may be related to, induced by, and/or caused by an injury, such as a radiation-induced injury, or a therapy (e.g., chemotherapy or radiotherapy) induced injury. As an example, the chemotherapy may comprise 5-fluorouracil. However, it may be any therapy that might lead to a hematopoietic disorder, injury and/or dysfunction.

Methods for Expanding/Enhancing HSPCs

In another aspect, the present application provides a method for one or more of the following:

1) increasing HSPC cell number;
2) expanding HSPCs;
3) promoting self-renewal of HSPC;
4) increasing a regenerative potential of HSPC;
5) improving a hematopoietic function of HSPC; and
6) maintaining and/or increasing quiescence of HSPC.

The method may comprise attenuating an expression and/or function of SphK2 of the HSPC.

In some cases, the method is an in vitro method. In some cases, the method is an in vivo method. In some cases, the method is an ex vivo method.

An increase in the number of HSPCs may refer to an increase of at least one HSPC, about at least a 10% increase, about at least a 20% increase, about at least a 30% increase, about at least a 40% increase, about at least a 50% increase, about at least a 60% increase, about at least a 70% increase, about at least a 80% increase, about at least a 90% increase, about at least a 100% increase, about at least a 1.5 fold increase, about at least a 2 fold increase, about at least a 2.5 fold increase, about at least a 3 fold increase, about at least a 3.5 fold increase, about at least a 4 fold increase, about at least a 4.5 fold increase, or greater. The increase of HSPCs may be measured indirectly by counting the number of cells positive for certain characteristic markers.

In some cases, an increase of the number of LT-HSCs are achieved with the methods of the present application. For example, the LT-HSCs may be detected as $CD34^-Flk^-Lin^-Sca1^+c\text{-}KIT^+$. The number of LT-HSCs may be increased by a least one cell, by at least about 10%, by at least about 20%, by at least about 30%, by at least about 40%, by at least about 50%, by at least about 60%, by at least about 70%, by at least about 80%, by at least about 90%, by at least about 100%, by at least about 1.5 fold, by at least about 2 fold (such as at least about 2-3 fold, such as at least about 2-2.5 fold), by at least about 2.5 fold, by at least about 3 fold, by at least about 3.5 fold, by at least about 4 fold, by at least about 4.5 fold, or greater.

In some cases, an increase of the number of ST-HSCs are achieved with the methods of the present application. For example, the ST-HSCs may be detected as $CD34^-Flk^+Lin^-Sca1^+c\text{-}KIT^+$. The number of ST-HSCs may be increased by a least one cell, by at least about 10%, by at least about 20%, by at least about 30%, by at least about 40%, by at least about 50%, by at least about 60%, by at least about 70%, by at least about 80%, by at least about 90%, by at least about 100%, by at least about 1.5 fold (such as at least about 1-2 fold, such as at least about 1-1.5 fold, such as about at least about 1.9 fold), by at least about 2 fold; by at least about 2.5 fold, by at least about 3 fold, by at least about 3.5 fold, by at least about 4 fold, by at least about 4.5 fold, or greater.

In some cases, an increase of the number of multipotent progenitor cells (MPPs) are achieved with the methods of the present application. For example, the MPPs may be detected as $CD34^+Flk^+Lin^-Sca1^+c\text{-}KIT^+$. The number of MPPs may be increased by a least one cell, by at least about 10%, by at least about 20%, by at least about 30%, by at least about 40%, by at least about 50%, by at least about 60%, by at least about 70%, by at least about 80%, by at least about 90%, by at least about 100%, by at least about 1.5 fold (such as at least about 1-2 fold, such as at least about 1-1.5 fold, such as about at least about 1.7 fold), by at least about 2 fold, by at least about 2.5 fold, by at least about 3 fold, by at least about 3.5 fold, by at least about 4 fold, by at least about 4.5 fold, or greater.

In some cases, an increase of the number of $CD150^+$ HSCs are achieved with the methods of the present application. For example, the $CD150^+$ HSCs may be detected as $CD150^+$ $CD48^-Lin^-Sca1^+c\text{-}KIT^+$. The number of $CD150^+$ HSCs may be increased by a least one cell, by at least about 10%, by at least about 20%, by at least about 30%, by at least about 40%, by at least about 50%, by at least about 60%, by at least about 70%, by at least about 80%, by at least about 90%, by at least about 100%, by at least about 1.5 fold, by at least about 2 fold (such as at least about 2-3 fold, such as at least about 2-2.5 fold), by at least about 2.5 fold, by at least about 3 fold, by at least about 3.5 fold, by at least about 4 fold, by at least about 4.5 fold, or greater.

The method of the present application may comprise administering an agent attenuating the expression and/or function of SphK2 (e.g., an inhibitor of SphK2) to the HSPC, for example, by contacting such an agent with a starting cell population (e.g., an unattenuated population of cells) comprising HSPCs.

The attenuated population of HSPCs may be administered to a subject. In some cases, the subject may be the same subject from which the unattenuated population of HSPCs was derived.

The method of the present application may comprise: (a) providing a starting cell population comprising HSPCs and (b) culturing said starting cell population in vitro or ex vivo in presence of an agent capable of attenuating the expression and/or activity of SphK2.

The cell population may first be subjected to enrichment or purification steps, including negative and/or positive selection of cells based on specific cellular markers in order to provide the starting cell population. Methods for isolating said starting cell population based on specific cellular markers may use fluorescent activated cell sorting (FACS) technology also called flow cytometry or solid or insoluble substrate to which is bound antibodies or ligands that interact with specific cell surface markers.

The starting cell population may be derived from bone marrow of a subject and/or a donor. The expansion or culturing of HSPCs may be carried out in a basal medium, which is supplemented with the mixtures of cytokines and growth factors.

The starting cell population may be cultured during a time sufficient to reach an absolute number of HSCs of at least $10^4$, $10^5$, $10^6$, $10^7$, $10^8$, $10^9$ or more cells. In some embodiments, the starting cell population may be cultured during a time sufficient for a 10 to 50000 fold expansion of the HSPCs, for example between 100 and 10000 fold expansion. The cell population obtained after the attenuation may be used without further purification or may be subjected to further purification or selection steps. The cell population may then be washed to remove the attenuating agent and/or any other components of the cell culture and resuspended in an appropriate cell suspension medium for short term use or in a long-term storage medium, for example a medium suitable for cryopreservation.

The starting cells may be, for example, from a bone marrow donor or an individual with or at risk for depleted or limited blood cell levels. The subject may be a bone marrow donor prior to bone marrow harvesting or a bone marrow donor after bone marrow harvesting.

HSPC manipulation may be used as a supplemental treatment to chemotherapy or radiation therapy. For example, HSPCs may be isolated from a subject that will undergo chemotherapy, and after the therapy the cells are returned. Thus, the subject is a subject undergoing or expected to undergo an immune cell depleting treatment such as chemotherapy, radiation therapy or serving as a donor for a bone marrow transplant. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy.

HSPCs or blood cells prepared by the methods described herein may be administered to such subjects in need of additional blood cells.

HSPCs and Pharmaceutical Compositions

In another aspect, the present application provides HSPCs obtained, prepared and/or manipulated by a method of the present application.

In another aspect, the present application provides an isolated HSPCs, or population of isolated HSPCs, wherein an expression and/or function of SphK2 of the HSPC is attenuated.

The isolated HSPCs may be modified (e.g., in vitro or ex vivo modified) to attenuate the expression and/or function of the SphK2 therein.

The present application also provides a cell population with manipulated HSPCs (e.g., with attenuated expression and/or function of SphK2), obtainable or obtained by a method of the present application. In some embodiments, such cell population is resuspended in a pharmaceutically acceptable medium suitable for administration to a mammalian host, thereby providing a pharmaceutical composition.

The present application also provides a pharmaceutical composition comprising the HSPCs or HSPC population according to the present application, and optionally a pharmaceutically acceptable carrier.

The present application also provides use of the HSPCs or the pharmaceutical composition according to the present application in the manufacture of a medicament for preventing, treating and/or alleviating a disease or disorder related to hematopoietic dysfunction and/or hematopoietic injury in a subject in need thereof, and/or for promoting hematopoietic recovery after bone marrow transplantation in a subject in need thereof.

The pharmaceutical composition may contain a total amount of cells of at least $10^4$, at least $10^5$, at least $10^6$, at least $10^7$, at least $10^8$, at least $10^9$, or more cells, with between about 20-100%, for example between about 40-80% of total cells being HSPC cells.

The pharmaceutically acceptable carrier may comprise a material that is not biologically or otherwise undesirable, i.e., the material may be administered to a subject or cell, without causing undesirable biological effects or interacting in a deleterious manner with the other components of the pharmaceutical composition in which it is contained. The carrier or excipient is selected to minimize degradation of the active ingredient and to minimize adverse side effects in the subject or cell.

Methods and Systems of Candidate Drug Screening

In another aspect, the present application provides a method and/or system for screening a candidate agent that may be used to prepare a medicament. The medicament may be used for preventing, treating and/or alleviating the disease or disorder related to hematopoietic dysfunction and/or hematopoietic injury, according to the present application.

The method may comprise evaluating a candidate agent for its ability to attenuate an expression and/or function of SphK2.

In some embodiments, the method comprises:

1) administering a candidate agent to a cell and/or an organism expressing SphK2 (e.g., ex vivo, or in vitro);
2) evaluating an effect of said candidate agent on the expression and/or activity of the SphK2; and
3) identifying the candidate agent attenuating the expression and/or activity of the SphK2 as an agent that may be used for preparing the medicament. The medicament may be used for preventing, treating and/or alleviating the disease or disorder related to hematopoietic dysfunction and/or hematopoietic injury, according to the present disclosure.

The system for screening a candidate agent that may be used to prepare the medicament may comprise: an organism and/or cell expressing SphK2. The system may also comprise an agent capable of detecting and/or indicating an attenuation of the expression and/or activity of SphK2, e.g., an antibody specifically binding to SphK2, or a probe specifically recognizing SphK2.

Attenuation of SphK2

According to any aspect of the present application, the expression and/or function of the SphK2 may be attenuated by inhibiting an expression and/or function of the SphK2 gene, and/or inhibiting an expression and/or function of the SphK2 protein.

In some cases, the expression and/or function of SphK2 may be attenuated genetically, e.g., by knocking out or knocking down the SphK2 gene. Alternatively or additionally, the expression and/or function of SphK2 may be attenuated with an inhibitor of SphK2.

For example, the attenuation may be achieved with a small interference RNA (siRNA) molecule capable of down-regulating the expression of SphK2, an antisense oligonucleotide capable of down-regulating the expression of SphK2, an antibody capable of inhibiting the activity of SphK2, and/or a small molecule inhibitor of SphK2.

Design of antisense oligonucleotides which can be used to efficiently inhibit the SphK2 protein expression must be effected in a way that such oligonucleotides specifically binds the designated mRNA within cells in a way which inhibits translation thereof. Sequence suitable for use in design and synthesis of antisense oligonucleotides which specifically bind to SphK2 mRNA, genomic DNA and/or its promoter or other control sequences are available in published sequence of SphK2, in particular human SphK2. In addition, algorithms for identifying sequences with the highest predicted binding affinity for their target mRNA based on thermodynamic cycle that accounts for the energetics of structural alterations in both the target mRNA and the oligonucleotides are also available.

In some cases, the expression and/or function of the SphK2 may be attenuated with a SphK2 inhibitor. The SphK2 inhibitor may be a small molecule inhibitor.

In some embodiments, the SphK2 inhibitor may be as described in WO2006138660A2, which is incorporated herein by reference in its entirety.

In some embodiments, the SphK2 inhibitor is 3-(4-chlorophenyl)-N-(pyridinyl-4-ylmethyl) adamantane-1-carboxamide, which is also known as ABC294640, or a pharmaceutically acceptable salt thereof.

In some embodiments, the SphK2 inhibitor comprises a compound of formula (I) or a pharmaceutically salt thereof:

(I)

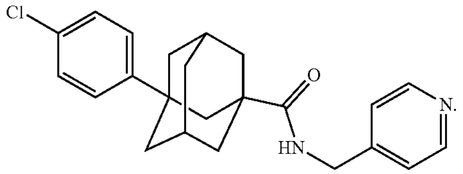

In some embodiments, the SphK2 inhibitor comprises a compound of formula (II) or a pharmaceutically acceptable salt thereof:

(II)

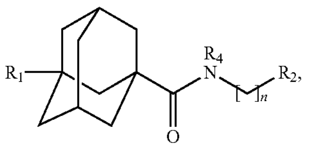

wherein:

$R_1$ is phenyl, or a phenyl substituted with a halogen;

$R_2$ is aryl, heteroaryl, or a substituted aryl or heteroaryl, such as a 4-pyridine;

$R_4$ is H or alkyl; and n is an integer of at least 1.

In some embodiments, the SphK2 inhibitor comprises a compound of formula (II) or a pharmaceutically acceptable salt thereof:

(II)

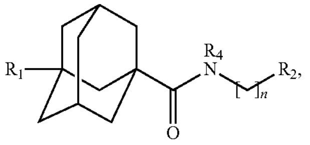

wherein:

$R_1$ is phenyl, 4-chlorophenyl or 4-fluorophenyl;

$R_2$ is 4-pyridyl, optionally substituted;

$R_4$ is H or alkyl; and n is 1 or 2.

In some embodiments, the SphK2 inhibitor comprises a compound of formula (III) or a pharmaceutically acceptable salt thereof:

(III)

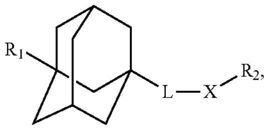

wherein:

L is a bond or an optionally substituted alkyl;

X is —C(O)N($R_4$)—;

$R_1$ is aryl (e.g., phenyl), heteroaryl, substituted aryl or substituted heteroaryl, in some cases, $R_1$ is aryl (e.g., phenyl) or heteroaryl substituted with a halogen (such as Cl), in some cases, $R_1$ is phenyl, 4-chlorophenyl or 4-fluorophenyl;

$R_2$ is aryl, -alkylaryl, heteroaryl, -alkyl-heteroaryl, substituted aryl, substituted -alkylaryl, substituted heteroaryl, or substituted -alkyl-heteroaryl; and $R_4$ is H or alkyl, such as ($C_1$-$C_6$) alkyl.

In some embodiments of the compounds of structural formula (III) as described above, $R_1$ is optionally substituted aryl, for example, phenyl. In some embodiments, the phenyl is unsubstituted. In other embodiments, the phenyl is substituted with a halogen (e.g., monohalo-substituted at the 4-position). For example, the halogen substituent may be Cl or F.

In some embodiments of the compounds of structural formula (III) as described above, $R_2$ is aryl or -alkylaryl.

In some embodiments of the compounds of structural formula (III) as described above, $R_2$ is heteroaryl or -alkyl-heteroaryl. In some cases, the alkyl is a methyl. In some cases, the heteroaryl is a pyridine. In some cases, $R_2$ is a -methyl-pyridine.

The present application also provides the following embodiments:

1. A method for preventing, treating and/or alleviating a disease or disorder related to hematopoietic dysfunction and/or hematopoietic injury in a subject in need thereof, comprising attenuating an expression and/or function of SphK2 in said subject.

2. The method of embodiment 1, comprising attenuating an expression and/or function of SphK2 in a hematopoietic stem cell and/or progenitor cell (HSPC) in said subject.

3. The method of embodiment 2, wherein said HSPC is a bone marrow derived HSPC.

4. A method for preventing, treating and/or alleviating a disease or disorder related to hematopoietic dysfunction and/or hematopoietic injury in a subject in need thereof, comprising administering to said subject an HSPC, wherein an expression and/or function of SphK2 of said HSPC is attenuated.

5. A method for preventing, treating and/or alleviating a disease or disorder related to hematopoietic dysfunction and/or hematopoietic injury in a subject in need thereof, comprising administering to said subject an HSPC, wherein said HSPC is derived from a donor with attenuated expression and/or functions of SphK2.

6. The method of any one of embodiments 1 to 5, wherein said disease or disorder related to hematopoietic dysfunction and/or hematopoietic injury comprises poor hemogram index, reduction of immune cells, reduction of white blood cells, reduction of platelets, and/or a bone marrow failure syndrome.

7. The method of any one of embodiments 1 to 6, wherein said disease or disorder is primary.

8. The method of any one of embodiments 1 to 7, wherein said disease or disorder is related to and/or caused by radiation or a therapy-induced injury.

9. The method of embodiment 8, wherein said therapy-induced injury comprises a radiotherapy-induced injury and/or a chemotherapy-induced injury.

10. The method of embodiment 9, wherein said chemotherapy comprises 5-fluorouracil.

11. A method for increasing hematopoietic cell expansion in a subject in need thereof, comprising attenuating an expression and/or function of SphK2 in said subject.

12. The method of embodiment 11, comprising attenuating an expression and/or function of SphK2 in an HSPC in said subject.

13. The method of embodiment 12, wherein said HSPC is a bone marrow derived HSPC.

14. A method for promoting hematopoietic recovery after bone marrow transplantation in a subject in need thereof, comprising attenuating an expression and/or function of SphK2 in said subject.

15. The method of embodiment 14, wherein said expression and/or function of SphK2 is attenuated in said subject after said bone marrow transplantation.

16. A method for promoting hematopoietic recovery after bone marrow transplantation in a subject in need thereof, comprising attenuating an expression and/or function of SphK2 in a HSPC of said bone marrow being transplanted.

17. A method for promoting hematopoietic recovery after bone marrow transplantation in a subject in need thereof, wherein said bone marrow is derived from a donor with attenuated expression and/or function of SphK2.

18. A method for promoting hematopoietic recovery after bone marrow transplantation in a subject in need thereof, wherein said transplanted bone marrow comprises an HSPC with attenuated expression and/or function of SphK2.

19. The method of any one of embodiments 14-17, wherein said hematopoietic recovery comprises a recovery of white blood cell number after said bone marrow transplantation, a recovery of platelet number after said bone marrow transplantation, a recovery from hematopoietic dysfunction after said bone marrow transplantation, an expansion of HSPC number after said bone marrow transplantation, an improvement of a hematopoietic function of an HSPC after said bone marrow transplantation, an enhancement of blood cell generation by an HSPC after said bone marrow transplantation, an increase of platelet number after said bone marrow transplantation, and/or an increase of blood immune cell number after said bone marrow transplantation.

20. The method of any one of embodiments 1-19, wherein said subject has been subjected to chemotherapy.

21. The method of embodiment 20, wherein said chemotherapy comprises 5-fluorouracil.

22. The method of any one of embodiments 1-21, wherein said subject has been subjected to radiation.

23. The method of embodiment 22, wherein said radiation comprises radiotherapy.

24. The method of any one of embodiments 1-23, wherein said subject has received bone marrow transplantation.

25. A method for increasing HSPC number, comprising attenuating an expression and/or function of SphK2 of said HSPC.

26. A method for expanding HSPC, comprising attenuating an expression and/or function of SphK2 of said HSPC.

27. A method for promoting a self-renewal activity of an HSPC, comprising attenuating an expression and/or function of SphK2 of said HSPC.

28. A method for increasing a regenerative potential of an HSPC, comprising attenuating an expression and/or function of SphK2 of said HSPC.

29. A method for improving a hematopoietic function of an HSPC, comprising attenuating an expression and/or function of SphK2 of said HSPC.

30. A method for maintaining and/or increasing quiescence of an HSPC, comprising attenuating an expression and/or function of SphK2 of said HSPC.

31. The method of any one of embodiments 25 to 30, which is an in vitro or ex vivo method.

32. An HSPC, obtained from a method according to any one of embodiments 25 to 31.

33. An isolated HSPC, wherein an expression and/or function of SphK2 of said HSPC is attenuated.

34. The isolated HSPC of embodiment 33, wherein said HSPC has been modified to attenuate the expression and/or function of SphK2 therein.

35. A pharmaceutical composition, comprising said HSPC of any one of embodiments 32 to 34, and optionally a pharmaceutically acceptable carrier.

36. The method of any one of embodiments 1 to 31, the HSPC of any one of embodiments 32 to 34, or the pharmaceutical composition of embodiment 35, wherein said expression and/or function of said SphK2 is attenuated by inhibiting an expression and/or function of the SphK2 gene, and/or inhibiting an expression and/or function of the SphK2 protein.

37. The method of any one of embodiments 1 to 31, the HSPC of any one of embodiments 32 to 34, or the pharmaceutical composition of embodiment 35, wherein said expression and/or function of said SphK2 is attenuated with a SphK2 inhibitor.

38. The method, the HSPC, or the pharmaceutical composition of embodiment 37, wherein said SphK2 inhibitor is a small molecule inhibitor.

39. The method, the HSPC, or the pharmaceutical composition of embodiment 37, wherein said SphK2 inhibitor comprises a compound of formula (I) or a pharmaceutically salt thereof:

(I)

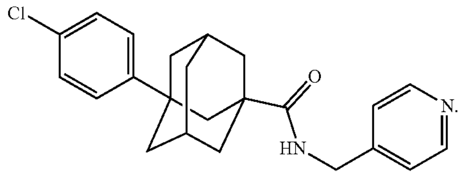 [SMILES: O=C(NCc1ccncc1)C12CC3CC(C1)CC(c1ccc(Cl)cc1)(C3)C2]

40. The method, the HSPC, or the pharmaceutical composition of embodiment 37, wherein said SphK2 inhibitor comprises a compound of formula (H) or a pharmaceutically acceptable salt thereof:

(II)

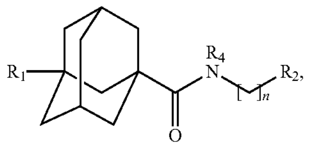

wherein: $R_1$ is phenyl, or a phenyl substituted with a halogen; $R_2$ is aryl, heteroaryl, or a substituted aryl or heteroaryl; $R_4$ is H or alkyl; and n is an integer of at least 1.

41. The method of any one of embodiments 1 to 31, the HSPC of any one of embodiments 32 to 34, or the pharmaceutical composition of embodiment 35, wherein said HSPC comprises a hematopoietic stem cell (HSC), a hematopoietic progenitor cell (HPC), a long-term HSC (LT-HSC), a short-term HSC (ST-HSC), a multipotent progenitor cell (MPP), and/or a CD150 HSC.

42. A method for screening a candidate agent for preventing, treating and/or alleviating a disease or disorder related to hematopoietic dysfunction and/or hematopoietic injury, said method comprising: determining an ability of said candidate agent in attenuating an expression and/or function of SphK2.

The technical solutions of the present application will be further illustrated in connection with the examples.

EXAMPLES

Example 1

It was demonstrated, by using SphK2 knockout mouse models, that attenuating SphK2 led to an increase of the number of hematopoietic stem cells in mouse bone marrow under normal physiological conditions.

SphK2 gene knockout mice (C57BL/6J) and SphK1 gene knockout mice (C57BL/6J) were obtained from the Jackson Laboratory of the United States, and were kept in a specific pathogen free (SPF) environment. First, six 6-8-week-old wild-type mice, six 6-8-week-old SphK1 gene knockout mice and six 6-8-week-old SphK2 gene knockout mice were selected and sacrificed by cervical dislocation. Femurs and tibias were taken and bone marrow was obtained from the bone marrow cavity with an 1 ml syringe. The bone marrow was dispersed to form single cell suspensions, and lysed with red blood cell lysis buffer for 2 min to remove red blood cells, followed by filtering through a 70 μm filter screen to obtain a single cell suspension.

In order to calculate the number of hematopoietic stem cells in mice, statistical quantification was performed for the number of hematopoietic stem cells using the molecular marker system $Lin^-Sca1^+c\text{-}Kit^+CD150^+CD48^-$, in combination with flow cytometry. Briefly, 2 million bone marrow cells were resuspended in 100 μl PBS, and 2 μl of a combination of anti-Lin, anti-Sca-1, anti-c-Kit, anti-CD150 and anti-CD48 was added. Samples were kept on ice for 1 h and washed with 1 ml of PBS, then resuspended with 300 μl of PBS for flow cytometry analysis to determine the number of hematopoietic stem cells in the mouse bone marrow. T-test analysis was carried out using Graphpad6.0, and the difference was considered statistically significant when $P<0.05$.

As shown in FIG. 1, under normal physiological conditions, the number of hematopoietic stem cells among bone marrow cells of the SphK2 gene knockout mice was significantly increased (***$P<0.001$) compared to the control group.

Figure 15:
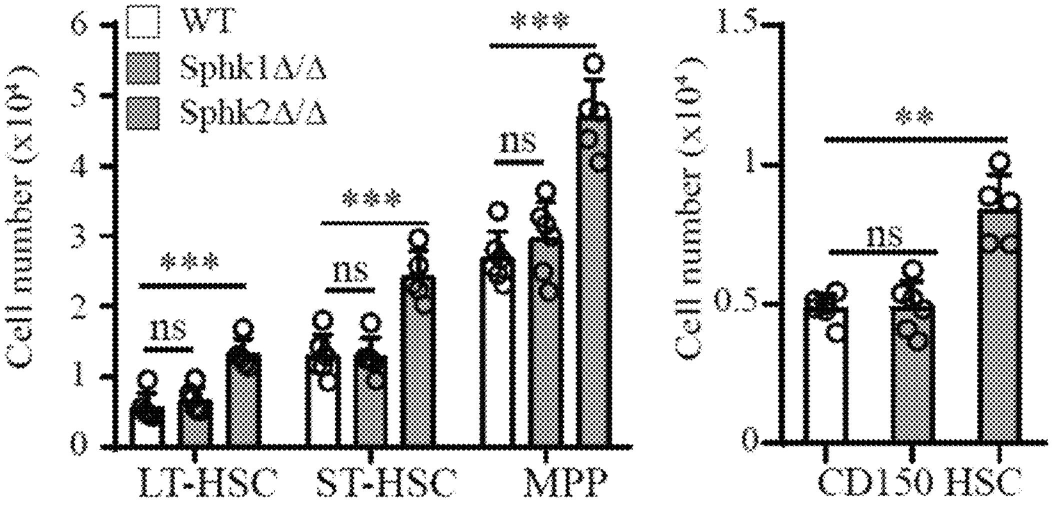
FIG. 15. illustrates the absolute number of HSPCs (LT-HSC, ST-HSC, MPP and CD150HSC) in the bone marrow from Sphk1 knockout ($Sphk1^{\Delta/\Delta}$) (n=6 mice), Sphk2 knockout ($Sphk2^{\Delta/\Delta}$) (n=5 mice) or control mice (WT) (n=6 mice).

Further, as shown in FIG. 15, an increase in the number of long-term HSCs (LT-HSCs, characterized as $CD34^-Flk^-Lin^-Sca1^+c\text{-}KIT^+$, with an increase of about 2.6 fold), short-term HSCs (ST-HSCs, characterized as $CD34^-Flk^+Lin^-Sca1^+c\text{-}KIT^+$, with an increase of about 1.9-fold), multipotent progenitor cells (MPPs, characterized as $CD34^+Flk^+Lin^-Sca1^+c\text{-}KIT^+$, with an increase of about 1.7-fold) and CD150 HSCs ($CD150^+CD48^-Lin^-Sca1^+c\text{-}KIT^+$, with an increase of about 2.5-fold) was observed in Sphk2 deficient mice but not in Sphk1 deficient mice.

Figure 16:
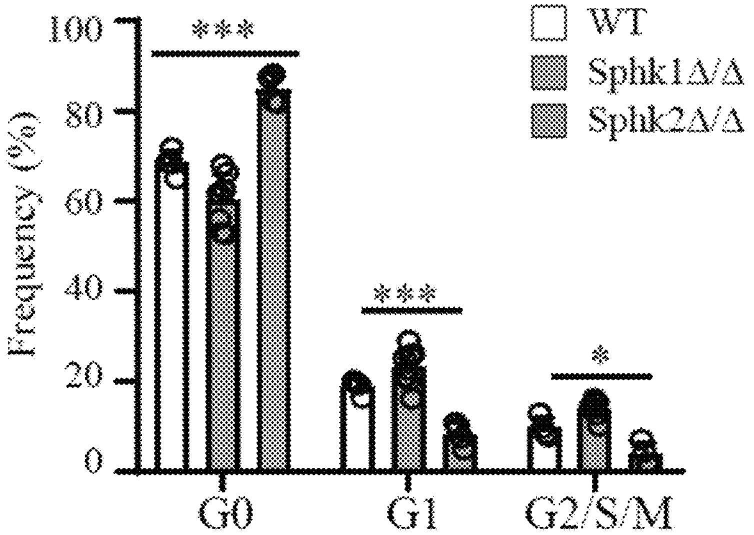
FIG. 16. illustrates the cell cycle analysis of CD150 HSCs in bone marrow from Sphk1 knockout (n=6 mice), Sphk2 knockout (n=5 mice) or control mice (WT) (n=6 mice).
Figure 17:
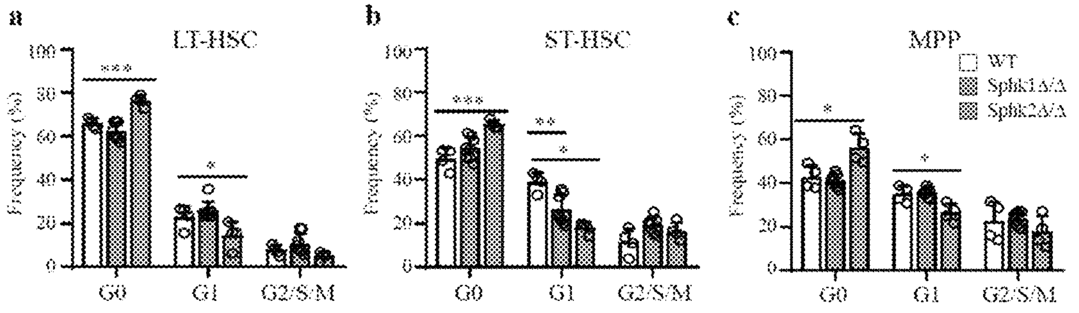
FIG. 17. illustrates the cell cycle analysis of LT-HSC, ST-HSC and MPP in the bone marrow from Sphk1 knockout (n=8 mice), Sphk2 knockout (n=4 mice) or control mice (WT) (n=4 mice). Data represent mean±s.d. Two-tailed Student's t-tests were used to assess statistical significance. *P<0.05, P<0.01, *P<0.001.

As shown by FIG. 16, the increased HSC numbers in Sphk2 deficient mice was not due to HSC activation because cell cycle analysis of CD150 HSCs revealed an increase in G0-phase fraction (from 68.4% to 84.9%) and concomitant decrease in the G1-phase fraction (from 18.7% to 8.1%) and the G2/S/M-phase fraction (from 9.6% to 3.6%) in Sphk2 deficient mice but not in Sphk1 deficient mice, when compared to control. The increase of G0-phase faction was also observed in LT-HSCs, ST-HSCs and MPPs in Sphk2 deficient mice (FIG. 17).

Example 2

Bone marrow hematopoietic injury was induced in mice with chemotherapy, such as 5-fluorouracil (5FU). It can be seen from FIG. 2 that the SphK2 knockout mice showed an enhanced recovery of the hematopoietic system after the chemotherapy induced injury.

Six 6-8-week-old wild-type mice and six 6-8-week-old SphK2 gene knockout mice as described in Example 1 were selected respectively, and injected intraperitoneally with 5FU (150 mg/kg body weight). 12 days later, these mice were sacrificed by cervical dislocation, and femurs and tibias were taken. The other sampling and analyzing processes were similar as described in Example 1.

Figure 2:
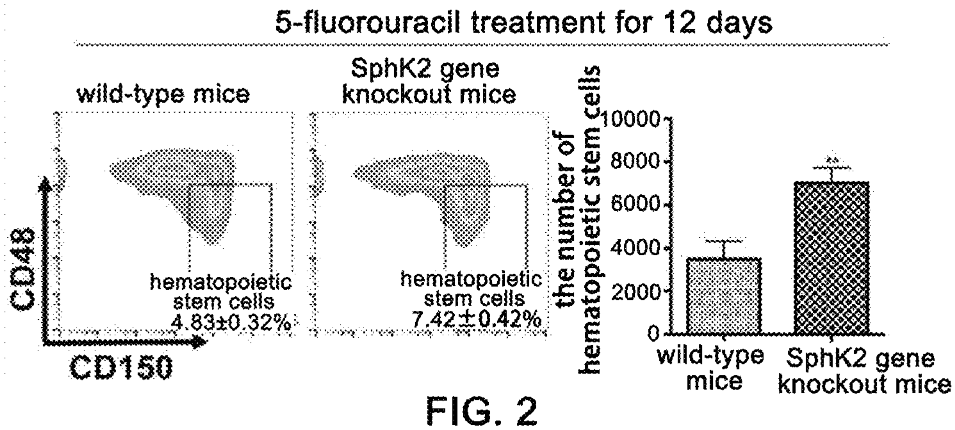
FIG. 2. SphK2 gene knockout accelerated post-injury repair of hematopoietic stem cells. Indicated in the box of the left graph was an increase of the proportion of hematopoietic stem cells in bone marrow of the wild-type mice and of the SphK2 gene knockout mice after subjected to the chemotherapeutic drug 5-fluorouracil; and the right graph showed the calculated number of hematopoietic stem cells in bone marrow cells of the wild-type mice and of the SphK2 gene knockout mice with 5-fluorouracil chemotherapy-induced injury, showing that the number of hematopoietic stem cells in the SphK2 gene knockout mice with chemotherapy-induced injury was significantly larger than that of the control group.

As shown by FIG. 2, with a stimulation with 5FU for 12 days, the number of hematopoietic stem cells among the bone marrow cells of SphK2 gene knockout mice was significantly higher than that of the wild-type mice. Accordingly, attenuation of SphK2 could indeed accelerate post-injury repair of the hematopoietic system (e.g., after bone marrow injury), and could be used for resisting chemotherapy-induced injury (**$P<0.01$).

Example 3

Compared with wild-type mice, survival period of SphK2 gene knockout mice was significantly prolonged after chemotherapy induced injury.

Ten 8-week-old wild-type mice and ten 8-week-old SphK2 gene knockout mice as described in Example 1 were selected respectively, and were injected intraperitoneally with 5FU at a dose of 150 mg/kg every 7 days for 3 consecutive weeks, and the survival period of the mice was monitored. Comparison of overall survival rates was performed using the Mantel_Cox log-rank test and differences were considered statistically significant when $P<0.05$.

Figure 3:
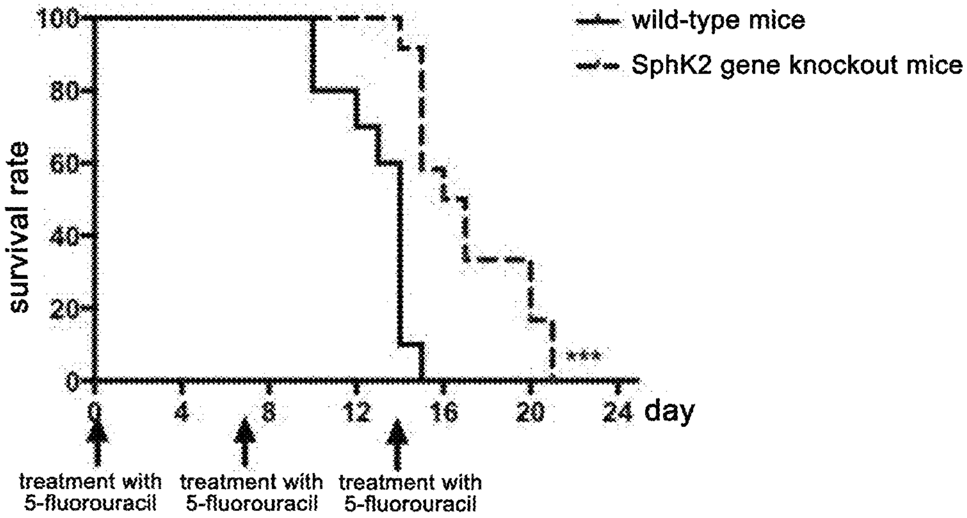
FIG. 3. The survivability of the SphK2 gene knockout mice was significantly enhanced after high-dose chemotherapy stimulation. Continuous 5-fluorouracil treatment resulted in rapid death in normal mice, but significant improvement in the survival rate of the SphK2 knockout mice was observed.

As shown by FIG. 3, comparing to wild-type mice, the survival period of the SphK2 gene knockout mice was remarkably (***$P<0.001$) prolonged after multiple 5FU treatments, indicating that attenuating SphK2 could lead to resistance to 5FU-induced chemotherapy injury.

To further test whether the increased survival is due to improved hematopoietic recovery, wide-type recipient mice were transplanted with Sphk2 deficient or control bone marrow cells and further challenged with multiple 5FU injections at 8 weeks after the transplantation. Briefly, 100 hematopoietic stem cells ($Lin^-Sca\text{-}1^+c\text{-}Kit^+CD150^+CD48^-$) from Sphk2 deficient mice or control donor mice were transplanted into lethally irradiated wide-type recipients along with $2\times10^5$ CD45.1 bone marrow cells. The mice were further challenged with multiple 5FU injections at 8 weeks after the transplantation.

Figure 25:
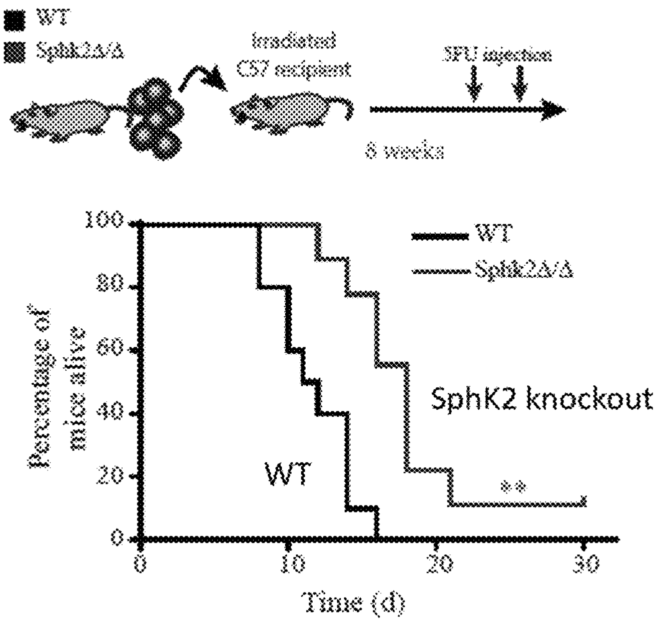
FIG. 25. illustrates the survival of Sphk2 knockout or control mice after serious 5FU treatment every 7 day (n=10 mice group).

Transplantation of Sphk2 deficient bone marrow cells significantly increased survival of the wild-type recipients compared to control bone marrow cells (P=0.001; FIG. 25), further demonstrating improved hematopoietic recovery due to Sphk2 deficiency.

Accordingly, attenuation of Sphk2 markedly promotes HSC expansion and function after chemotherapy-induced injury.

Example 4

Attenuating SphK2 with an inhibitor could effectively enhance the post-injury repair of hematopoietic stem cells after chemotherapy treatment.

Twenty 8-week-old C57 mice (purchased from Laboratory Animal Center, Sun Yat-sen University) were injected intraperitoneally with 5FU at a dose of 150 mg/kg, respectively. After 5FU treatment, control mice (10 mice) were injected with a solvent control solution (1:1 physiological saline: PEG400) and the SphK2 inhibitor treatment mice (10 mice) were injected with the SphK2 inhibitor ABC294640. Briefly, 5FU was injected on day 1, and the inhibitor and solvent control solution were injected on day 2 and every other day, for five times in total. On day 12, bone marrow cells were harvested, and the number of hematopoietic stem cells was determined, with the method and analysis as described in Example 1.

The SphK2 inhibitor ABC294640 was purchased from Selleck and dissolved in dimethyl sulfoxide (DMSO), it was then diluted with a mixture solution of polyethylene glycol 400 (PEG400) and physiological saline (1:1), and was injected to the mice with a dose of 10 mg/kg. T-test analysis was carried out using Graphpad6.0, and the differences were considered statistically significant when $P<0.05$.

Figure 4:
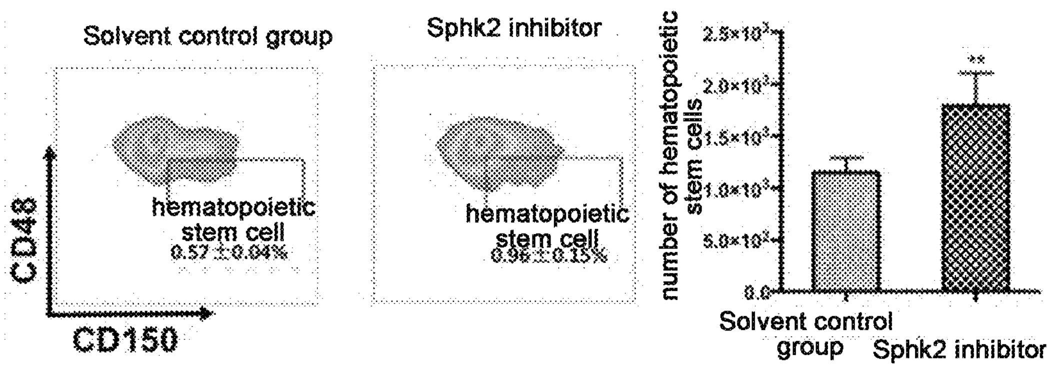
FIG. 4. The injection of the inhibitor ABC294640 resulted in a remarkable increase in the number of hematopoietic stem cells. Indicated in the box of the left graph was the proportion of hematopoietic stem cells in bone marrow cells in the mice of a solvent control group and of an ABC294640 treatment group after subjected to chemotherapeutic drug 5-fluorouracil, showing that compared with the mice in the solvent control group, the number of hematopoietic stem cells in the mice of the ABC294640 treatment group increased remarkably; and the right graph showed the calculated number of hematopoietic stem cells in bone marrow cells of the mice in the solvent control group and in the ABC294640 treatment group after subjected to the chemotherapeutic drug 5-fluorouracil, and the results showed that the number of hematopoietic stem cells in the treatment group increased significantly, indicating that ABC294640 remarkably promoted the post-injury repair of hematopoietic stem cells.

As shown by FIG. 4, after 5FU treatment, the number of hematopoietic stem cells was increased significantly (**$P<0.01$) in the mice treated with the SphK2 inhibitor.

Figure 26:
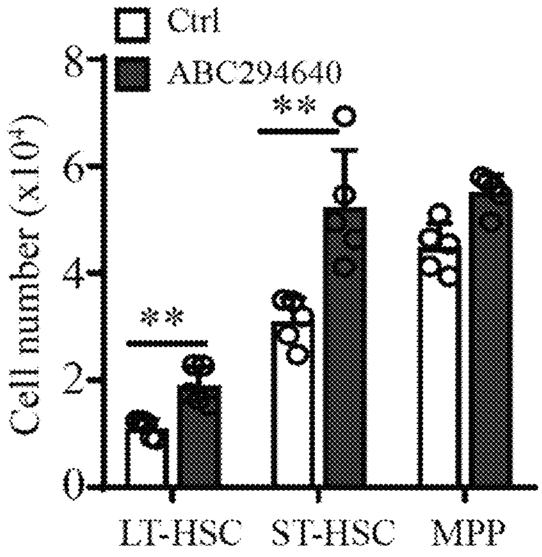
FIG. 26. illustrates HSPC (LT-HSC, ST-HSC, MPP, CD150HSC) numbers from C57BL/6J mice after 5FU and ABC294640 or solvent control treatment (n=5 mice).

Also, the mice treated with ABC294640 significantly increased HSC pool size (about 2.2-fold, about 1.6-fold, and about 2.2-fold increase for LT-HSC, ST-HSC and CD150 HSC respectively; FIG. 26) compared to mice treated with the solvent control at day 14 post 5FU treatment.

These results indicate that SphK2 inhibitors could effectively enhance the self-renewal ability and post-injury repair speed of hematopoietic stem cells. Accordingly, the SphK2 inhibitors could be used for treating hematopoietic dysfunction caused by chemotherapy-induced injury.

Example 5

SphK2 inhibitors significantly accelerated the recovery of white blood cells after chemotherapy treatment.

Preparation of the SphK2 inhibitor was as described in Example 4. Twelve 8-week-old C57 mice purchased from Laboratory Animal Center, Sun Yat-sen University were selected and divided evenly into two groups. The mice were intraperitoneally injected with 5FU at a dose of 150 mg/kg once. The injection of the inhibitor ABC294640 and the solvent control solution was as described in Example 4, which started from the day after 5-fluorouracil injection, followed by injections once every other day, at a dose of 10 mg/kg, until the end of the experiment. Periphery blood (PB) of each mouse was separately collected to determine white blood cell (WBC) counts 0, 1, 5 and 11 days after 5-FU administration. T-test analysis was carried out using Graphpad6.0, and differences were considered statistically significant when $P<0.05$.

Figure 5:
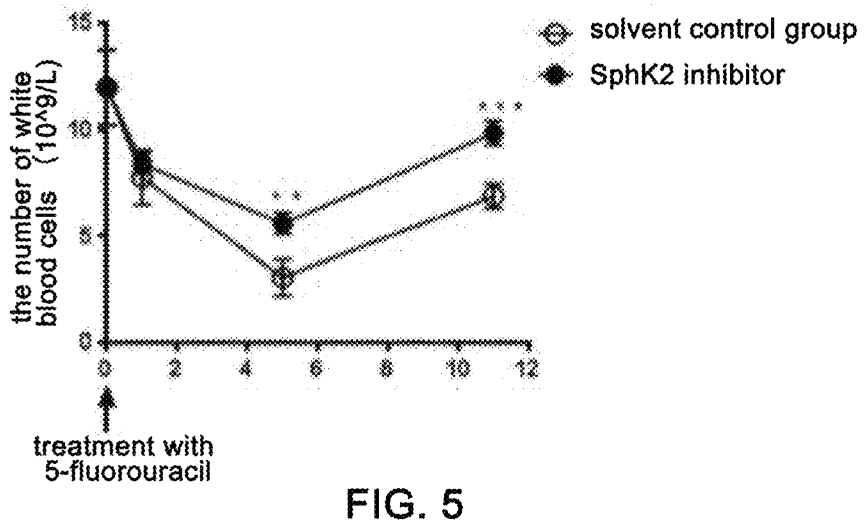
FIG. 5. The injection of the inhibitor ABC294640 significantly accelerated recovery of white blood cells after the stimulation of the chemotherapeutic drug 5-fluorouracil.

As shown by FIG. 5, comparing to the solvent solution control group, the number of white blood cells from the peripheral blood of the SphK2 inhibitor-treated mice was significantly increased ($P<0.01$, and *$P<0.001$), indicating that the SphK2 inhibitor could effectively improve chemotherapy induced injuries, such as hematopoietic dysfunction and immune cell reduction.

Example 6

SphK2 inhibitors significantly accelerated the recovery of platelets after chemotherapy treatment.

The experiment was conducted as described in Example 5. Periphery blood (PB) of each mouse was separately collected to determine platelets (PLT) counts 0, 1, 5 and 11 days after 5-FU administration. T-test analysis was carried out using Graphpad6.0, and differences were considered statistically significant when $P<0.05$.

Figure 6:
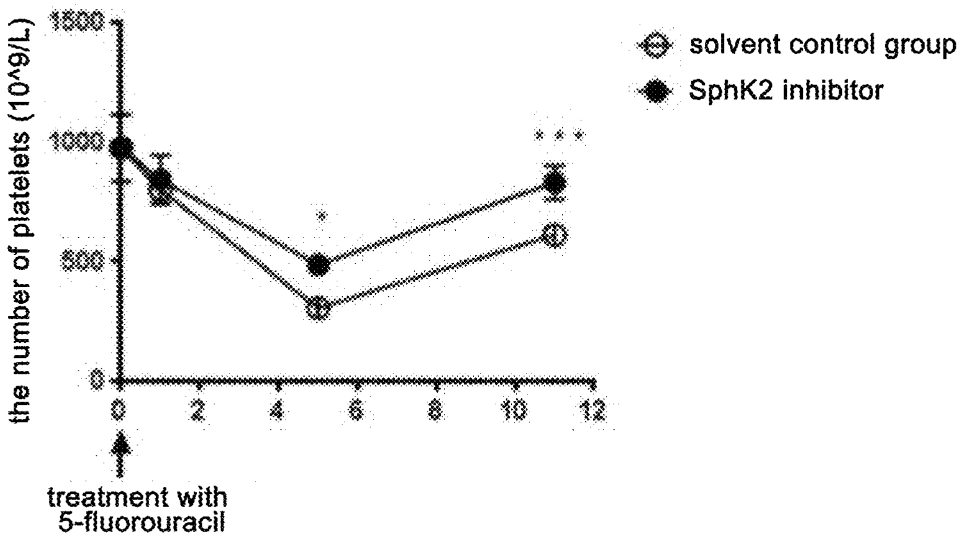
FIG. 6. The injection of the inhibitor ABC294640 significantly accelerated recovery of platelets after the stimulation of the chemotherapeutic drug 5-fluorouracil.

As show in FIG. 6, comparing to the solvent solution control group, the number of platelets from the peripheral blood of the ABC294640-treated mice was significantly increased (*$P<0.05$, and ***$P<0.001$), indicating that SphK2 inhibitors could effectively promote recovery of platelets after chemotherapy treatment.

Example 7

SphK2 inhibitors significantly accelerated recovery of white blood cells after radiation injury.

Preparation of SphK2 inhibitors was as described in Example 4. Twelve 8-week-old C57 mice purchased from Laboratory Animal Center, Sun Yat-sen University were selected and divided evenly into two groups. The mice were treated with X-ray radiation at a dose of 450 cGy. The injection of the inhibitor ABC294640 and the solvent control solution was as described in Example 4. Intraperitoneal injection of the inhibitor or the solvent control solution started from the day after the X-ray radiation, followed by injections once every other day, at a dose of 10 mg/kg, until the end of the experiment. Periphery blood (PB) of each mouse was separately collected to determine white blood cell (WBC) counts 0, 1, 7 and 14 days after X-ray radiation. T-test analysis was carried out using Graphpad6.0, and differences were considered statistically significant when $P<0.05$.

Figure 7:
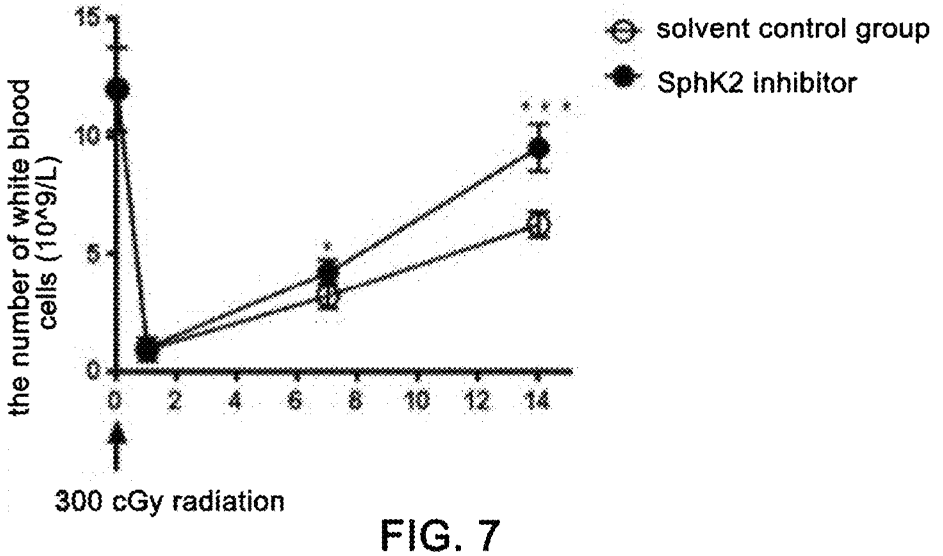
FIG. 7. The injection of the inhibitor ABC294640 significantly accelerated recovery of white blood cells after the stimulation of radiation.

As shown in FIG. 7, comparing to the solvent solution control group, the number of white blood cells from the peripheral blood of the ABC294640 treated mice was significantly increased (*$P<0.5$, and ***$P<0.001$), indicating that SphK2 inhibitors could effectively accelerate the recovery of WBCs in the peripheral blood. Accordingly, these results suggest that SphK2 inhibitors could be used for treating hematopoietic dysfunction caused by radiation induced injury.

Example 8

SphK2 inhibitors significantly accelerated the recovery of platelets after radiation-induced injury.

The experiment was conducted as described in Example 7. Periphery blood (PB) of each mouse was separately collected to determine platelets (PLT) counts 0, 1, 7 and 14 days after X-ray radiation. T-test analysis was carried out using Graphpad6.0, and differences were considered statistically significant when $P<0.05$.

Figure 8:
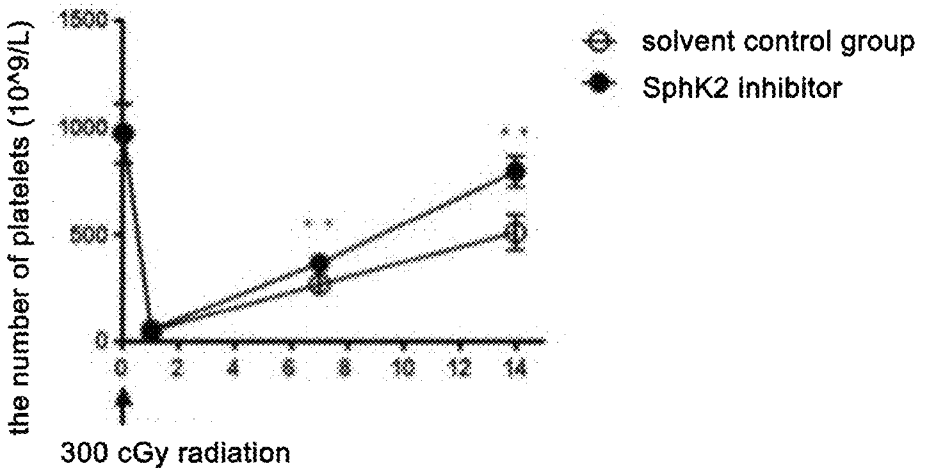
FIG. 8. The injection of the inhibitor ABC294640 significantly accelerated recovery of platelets after the stimulation of radiation.

As shown in FIG. 8, comparing to the solvent solution control group, the number of platelets in the peripheral blood of ABC294640-treated mice was significantly increased (**$P<0.01$), indicating that SphK2 inhibitors could be used for treating hematopoietic dysfunction related to radiation induced injury, such as platelet decrease related to radiation induced injury.

Example 9

SphK2 inhibitors could effectively increase the survival rate of mice after repeated high-dose chemotherapy treatment.

Figure 9:
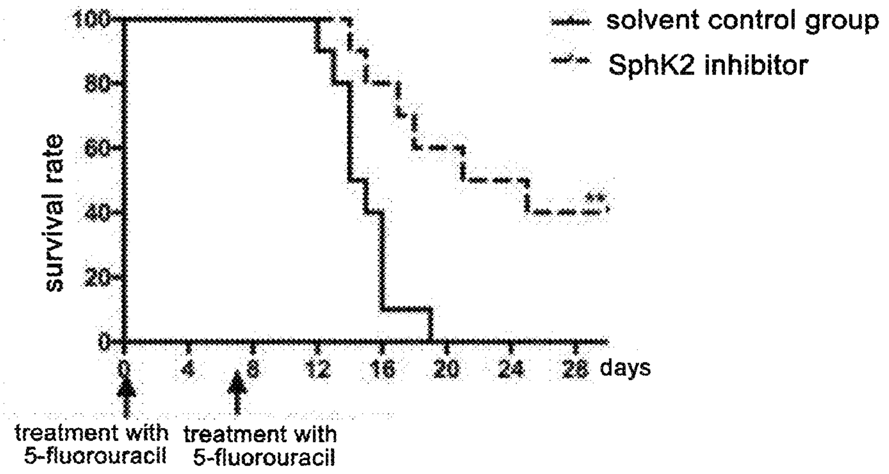
FIG. 9. The survivability of the mice injected with the inhibitor ABC294640 was significantly enhanced under multiple 5-fluorouracil stimulations.

Preparation of SphK2 inhibitors was as described in Example 4. 112 8-week-old C57 mice purchased from Laboratory Animal Center, Sun Yat-sen University were selected and divided evenly into two groups. The mice were intraperitoneally injected with 5FU at a dose of 150 mg/kg, once every 7 days for two times in total. The inhibitor ABC294640 was injected starting from the day after 5FU injection, then injected once every other day, at a dose of 10 mg/kg, until the end of the experiment. Mortality of the mice was recorded and the results are shown in FIG. 9. Comparison of overall survival rates was performed using the Mantel_Cox log-rank test and differences were considered statistically significant when $P<0.05$.

As shown in FIG. 9, comparing to the mice in the control group, the survival period of the ABC294640-treated mice was significantly (***$P<0.001$) prolonged after repeated high-dose chemotherapy treatment. Accordingly, SphK2 inhibitors could effectively resist chemotherapy-induced injuries.

Example 10

SphK2 inhibitors significantly increased the number of hematopoietic stem cells after bone marrow transplantation.

Twenty-five 8-week-old C57 mice (purchased from Laboratory Animal Center, Sun Yat-sen University) were selected and kept in a specific pathogen free (SPF) environment. 5 mice were randomly selected and sacrificed by cervical dislocation. Femurs and tibias were taken and the bone marrow was obtained from the bone marrow cavity with an 1 ml syringe. Bone marrow was dispersed to form a single cell suspension and lysed with red blood cell lysis buffer for 2 min to remove red blood cells, followed by filtering through a 70 μm filter screen to obtain a single cell suspension. The other 20 mice were treated with X-ray radiation at a dose of 900 cGy, and were injected with 400,000 of the prepared bone marrow single cell suspension via tail vein, respectively. Then, the recipient mice were divided evenly into 2 groups, and mice of the ABC294640 treatment group were subjected to intraperitoneal injection of ABC294640 every other day. Mice in the control group was injected with a solvent solution control (1:1 of physiological saline: PEG400) solution. ABC294640 was purchased from Selleck and dissolved in dimethyl sulfoxide (DMSO), and diluted with a mixture solution of polyethylene glycol 400 (PEG400) and physiological saline (1:1) to be administered at a dose of 10 mg/kg.

Briefly, the mice were radiated and subjected to bone marrow transplantation on day 0, then, ABC294640 and the control solvent solution were injected on day 1 and every other day. 35 days after transplantation, bone marrow cells were harvested from the mice of the control group and the ABC294640 treatment group. Statistical quantification was performed to determine the number of hematopoietic stem cells using the molecular marker system Lin-Sca-1+c-Kit+ CD150+CD48− in combination with flow cytometry. Briefly, 2 million bone marrow cells were resuspended in 1000 PBS, and 2 μl of a combination of anti-Lin, anti-Sca-1, anti-c-Kit, anti-CD150 and anti-CD48 antibodies was added. The samples were kept on ice for 1 h and washed with 1 ml of PBS and resuspended with 300 μl of PBS for flow cytometry analysis to determine the number of hematopoietic stem cells in the bone marrow of the mice. T-test analysis was carried out using Graphpad6.0, and differences were considered statistically significant when $P<0.05$.

Figure 10:
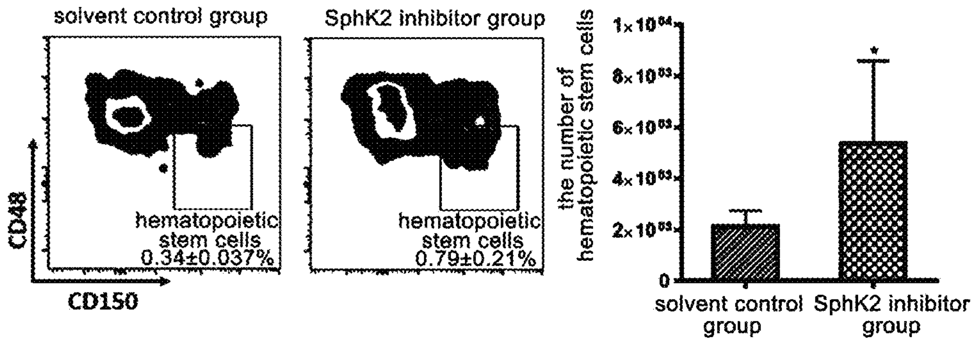
FIG. 10. The injection of the SphK2 gene inhibitor ABC294640 after hematopoietic stem cell bone marrow transplantation resulted in a remarkable increase in the number of hematopoietic stem cells.

As shown in FIG. 10, the number of hematopoietic stem cells increased remarkably (**$P<0.01$) in the mice of the ABC294640 treatment group after bone marrow transplantation, indicating that SphK2 inhibitors could effectively enhance the ability of hematopoietic stem cell self-renewal after bone marrow transplantation, and could be used to help subjects of bone marrow transplantation get through the critical period quickly after the transplantation.

Example 11

SphK2 inhibitors significantly accelerated the recovery of white blood cells after bone marrow transplantation.

Preparation of SphK2 inhibitors was as described in Example 10. Twenty 8-week-old C57 mice purchased from Laboratory Animal Center, Sun Yat-sen University were selected and divided evenly into two groups. Bone marrow transplantation and subsequent treatments with the SphK2 inhibitor and the control solution were as described in Example 10. Periphery blood (PB) of each mouse was collected to determine white blood cell (WBC) counts 7, 14, 21, 28 and 35 days after transplantation. T-test analysis was carried out using Graphpad6.0, and differences were considered statistically significant when $P<0.05$.

Figure 11:
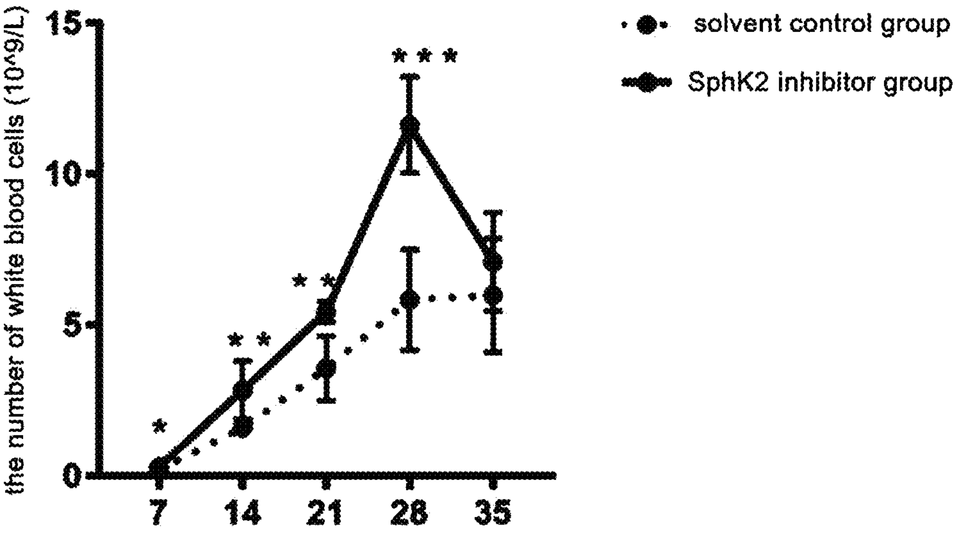
FIG. 11. The injection of the inhibitor ABC294640 significantly accelerated the recovery of platelets after hematopoietic stem cell bone marrow transplantation.

As shown in FIG. 11, comparing to the solvent solution control group, the number of white blood cells in the peripheral blood of the ABC294640 treatment group was significantly (*$P<0.05$, $P<0.01$ and *$P<0.001$) increased, indicating that SphK2 inhibitors could effectively enhance the differentiation ability of hematopoietic stem cells after bone marrow transplantation, and may be used to help subjects of bone marrow transplantation get through the critical period quickly after the transplantation.

Example 12

SphK2 inhibitors significantly accelerated the recovery of platelets after bone marrow transplantation.

Preparation of SphK2 inhibitors was as described in Example 10. Twenty 8-week-old C57 mice purchased from Laboratory Animal Center, Sun Yat-sen University were selected and divided evenly into two groups. Bone marrow transplantation and subsequent treatments with the SphK2 inhibitor and the control solution were as described in Example 10. Periphery blood (PB) of each mouse was collected to determine platelets (PLT) counts 7, 14, 21, 28 and 35 days after transplantation. T-test analysis was carried out using Graphpad6.0, and differences were considered statistically significant when $P<0.05$.

Figure 12:
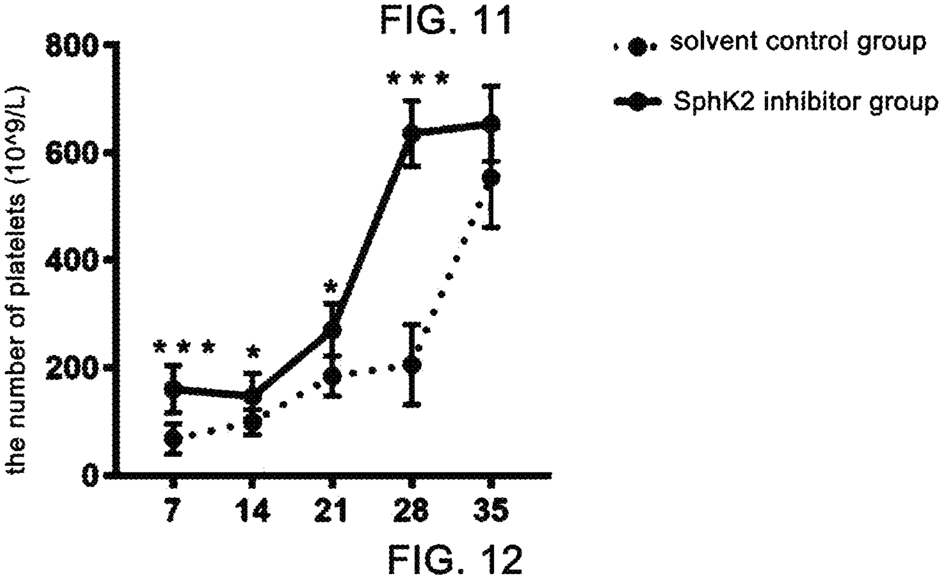
FIG. 12. The injection of the inhibitor ABC294640 significantly accelerated the recovery of white blood cells after hematopoietic stem cell bone marrow transplantation.

As shown in FIG. 12, comparing to the solvent solution control group, the number of platelets in the peripheral blood of the ABC294640 treatment group was significantly (*$P<0.05$, and ***$P<0.001$) increased, indicating that SphK2 inhibitors could effectively enhance the differentiation ability of hematopoietic stem cells after bone marrow transplantation, and may be used to help subjects of bone marrow transplantation get through the critical period quickly after the transplantation.

Example 13

To analyze whether Sphk2 deficient hematopoietic stem cells have increased hematopoietic function, 100 hematopoietic stem cells ($Lin^-Sca\text{-}1^+c\text{-}Kit^+CD150^+CD48^-$) from Sphk2 deficient mice or control donor mice were transplanted into irradiated wide-type recipients along with $2\times10^5$ CD45.1 bone marrow cells. Adult CD45.1 recipient mice were irradiated with an Orthovoltage X-ray source delivering approximately in two equal doses of 450 cGy at least 3 hours apart. Peripheral blood was collected from the tail vein every 4 weeks after the transplantation. Hematopoietic repopulation function was examined from donor-derived blood cells.

Figure 13:
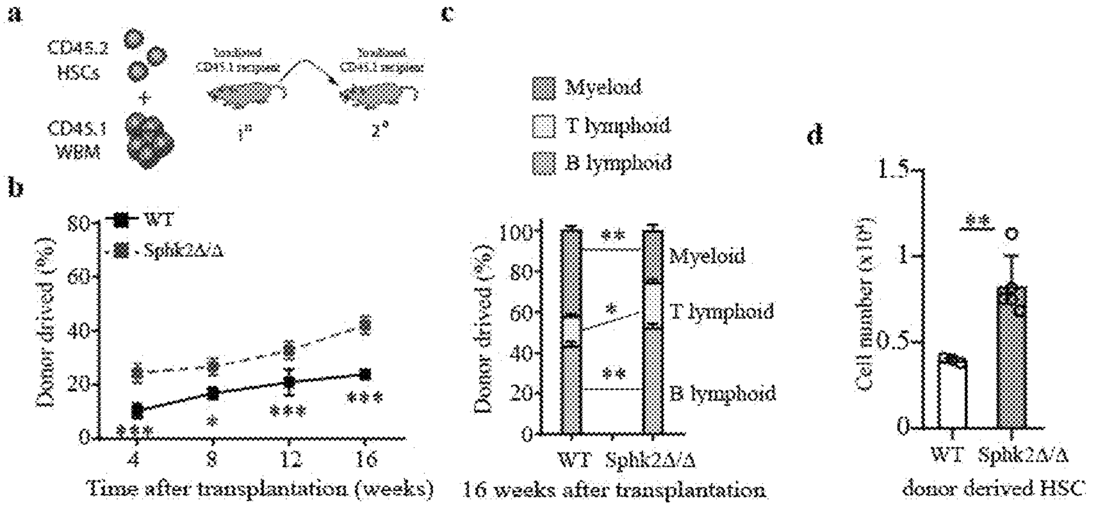
FIG. 13. SphK2 gene knockout led to an increase in the function of hematopoietic stem cells. Purified hematopoietic stem cells from wide type mice or Sphk2 deficient mice ($Sphk2^{\Delta/\Delta}$) were transplanted into irradiated recipient mice to evaluate the hematopoietic function of hematopoietic stem cells after Sphk2 gene knockout (a). Through 16-weeks observation, Sphk2 deficient hematopoietic stem cells gave significant higher reconstitution (b). Sphk2 deficient hematopoietic stem cells were able to give multi-hematopoietic lineage (c) and more donor derived hematopoietic stem cells (d). This demonstrated that Sphk2 gene knockout led to an increase in the function of hematopoietic stem cells.

As shown in FIG. 13, Sphk2 deficient hematopoietic stem cells significantly increased the levels of reconstitution than control cells through 16-week observation (2.3-fold increased at 16 weeks after transplantation, see panel b of FIG. 13). Sphk2 deficient hematopoietic stem cells were able to generate multi-hematopoietic lineage (panel c in FIG. 13) and more donor-derived hematopoietic stem cells (panel d in FIG. 13) in the recipients. T-test analysis was carried out using Graphpad6.0, and differences were considered statistically significant when $^*P<0.05$, $^{}P<0.01$ and $^{*}P<0.001$.

Figure 18:
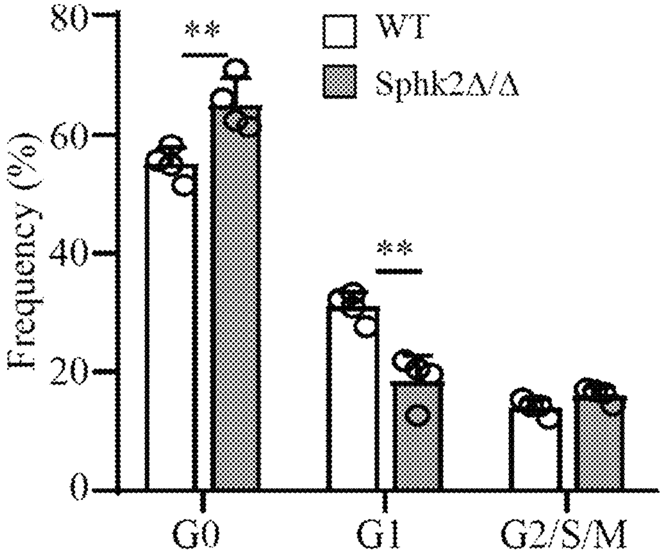
FIG. 18. illustrates the cell cycle analysis of CD150HSCs from Sphk2 knockout or control mice at day 7 after 5FU treatment. (n=4 mice).
Figure 19:
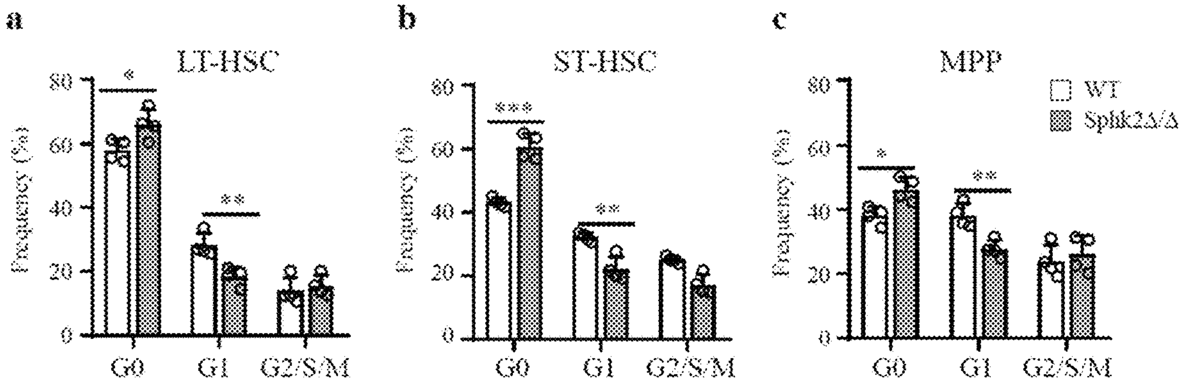
FIG. 19. illustrates the cell cycle analysis of LT-HSC, ST-HSC and MPP in the bone marrow from Sphk2 knockout or control mice (WT) at day 7 post 5FU treatment (n=4 mice). Data represent mean±s.d. Two-tailed Student's t-tests were used to assess statistical significance. *P<0.05, P<0.01, *P<0.001.
Figure 20:
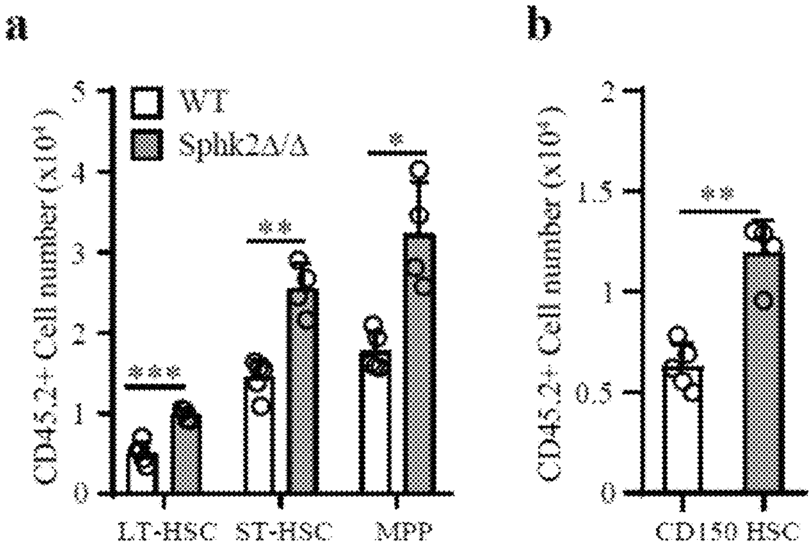
FIG. 20. illustrates the quantification of functional HSC regeneration by transplantation assay. $2\times10^5$ bone marrow cells from Sphk2 knockout or control mice at day 7 after 5FU treatment were transplanted into irritated mice along with $2\times10^5$ recipient bone marrow cells. The absolute numbers of donor derived HSPCs (CD45.2+; LT-HSC, ST-HSC, MPP and CD150HSC) in the bone marrow were analyzed at 16 weeks after transplantation. (WT n=5 mice, Sphk2 knockout n=4 mice). Data represent mean±s.d. Two-tailed Student's t-tests were used to assess statistical significance. *P<0.05, P<0.01, *P<0.001.

As shown in FIG. 18 and FIG. 19, Sphk2 deficient $CD150^+$ HSCs have increased G0-phase fraction (from 54.9% to 65.1%) and reduced G1-phase fraction (from 31.0% to 18.7%), which was also evidenced in LT-HSCs, ST-HSCs and MPPs. In addition, as shown in FIG. 20, comparing to wildtype control donors, significantly higher reconstitution (CD45.2) and donor derived HSCs from Sphk2 deficient bone marrow cells were observed.

Figure 21:
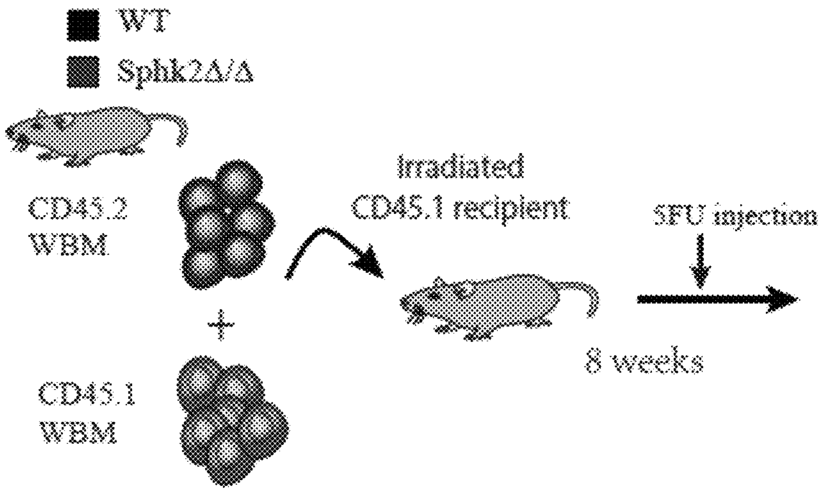
FIG. 21. illustrates the scheme for quantification of HSC function in response to chemotherapy by transplantation assay. $2\times10^5$ bone marrow cells from Sphk2 knockout or control mice were transplanted into irritated mice along with $2\times10^5$ recipient bone marrow cells. Recipient mice were treated with 5FU at 8 weeks after transplantation.

To assess whether Sphk2 deficient HSCs have improved regenerative capacity, recipient mice were challenged with 5FU at 8 weeks after the transplantation with Sphk2 deficient bone marrow cells or control donor cells along with recipient bone marrow cells (see FIG. 21).

Figure 22:
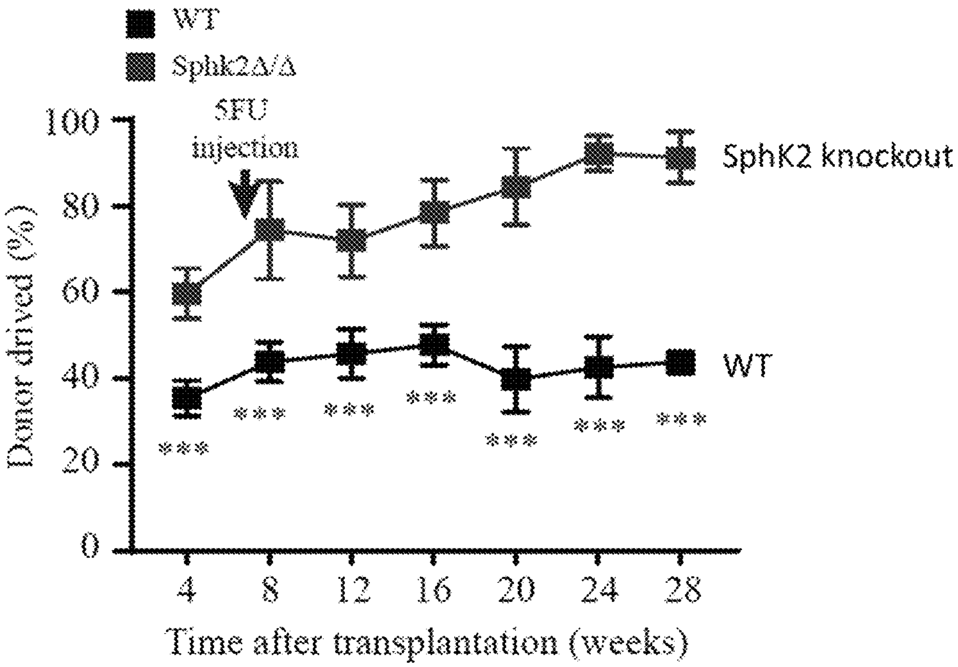
FIG. 22. illustrates the PB analysis for total engrafted donor cells at the indicated number of weeks after transplantation (WT n=6 mice, Sphk2Δ/Δ n=10 mice group).
Figure 23:
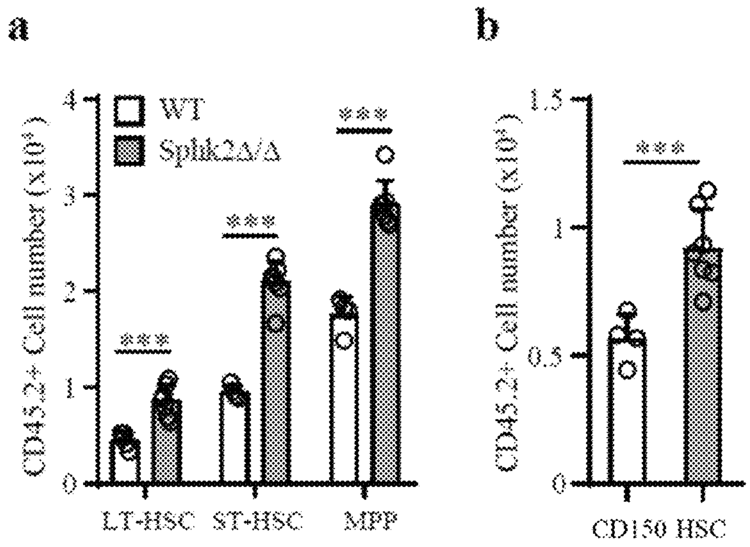
FIG. 23. illustrates the quantification of HSC function in response to chemotherapy by transplantation assay. $2\times10^5$ bone marrow cells from Sphk2 knockout or control mice were transplanted into irritated mice along with $2\times10^5$ recipient bone marrow cells. Recipient mice were treated with 5FU at 8 weeks after transplantation. The absolute numbers of donor derived HSPCs (CD45.2+; LT-HSC, ST-HSC, MPP and CD150HSC) in the bone marrow were analyzed at 16 weeks after 5FU treatment. (WT n=4 mice, Sphk2 knockout n=7 mice). Data represent mean±s.d. Two-tailed Student's t-tests were used to assess statistical significance. *P<0.05, P<0.01, *P<0.001.
Figure 24:
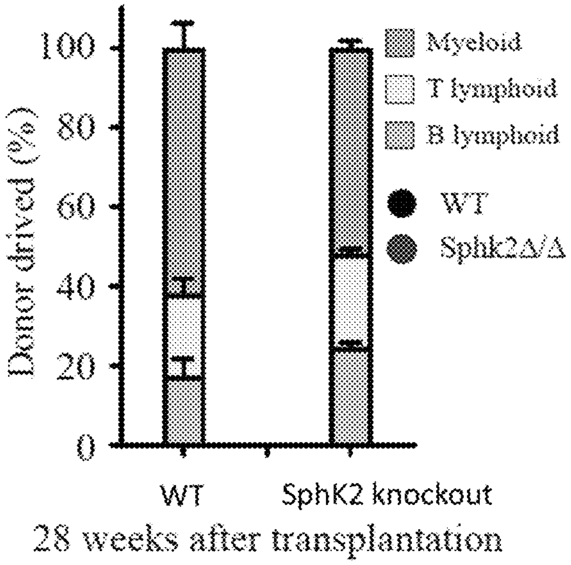
FIG. 24. illustrates the percentage of donor-derived B, T and myeloid lineage cells at 16 weeks after 5FU treatment (WT n=6 mice, Sphk2Δ/Δ n=10 mice group).

Consistently, Sphk2 deficient HSCs gave higher reconstitution (about 2-fold increase at 28 weeks, see FIG. 22), more donor derived HSCs (FIG. 23) and were capable of multi-lineage reconstitution (FIG. 24).

Example 14

To analyze whether Sphk2 inhibitor is effective in expanding hematopoietic stem cell number and enhance their function. Twenty 8-week-old C57 mice (purchased from Laboratory Animal Center, Sun Yat-sen University) were selected for the experiment. The mice were divided evenly into an inhibitor treatment group and a control group.

The mice were injected intraperitoneally with ABC294640 (inhibitor treatment group) or solvent control (1:1 physiological saline: PEG400) solution (control group) every other day. 14 days after the first injection, bone marrow cells were harvested from both groups, and were analyzed for the number of hematopoietic stem cells, with methods and analysis as described in Example 1.

To evaluate the hematopoietic function of the hematopoietic stem cells, $2\times10^5$ bone marrow cells from Sphk2 inhibitor or solvent control treated mice were transplanted into irradiated recipients (as described in Example 13). Peripheral blood was collected from the tail vein every 4 weeks after transplantation. The hematopoietic repopulation function was examined from donor-derived blood cells. The Sphk2 inhibitor was prepared as described in Example 4. Briefly, ABC294640 was purchased from Selleck and dissolved in dimethyl sulfoxide (DMSO), which was finally diluted with a mixture solution of polyethylene glycol 400 (PEG400) and physiological saline (1:1) to be administered at a dose of 10 mg/kg. T-test analysis was carried out using Graphpad6.0, and differences were considered statistically significant when $^*P<0.05$, $^{}P<0.01$ and $^{*}P<0.001$.

Figure 14:
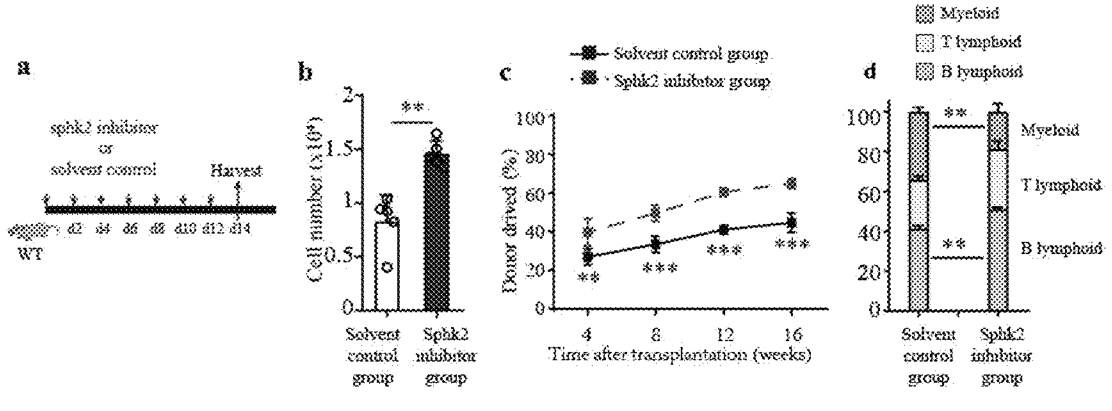
FIG. 14. The injection of the inhibitor ABC294640 resulted in increased hematopoietic stem cell number and function. Mice subjected to solvent control or Sphk2 inhibitor (ABC294640) treatment (a). Sphk2 inhibitor treatment markedly increased hematopoietic stem cell number (b) and promoted hematopoietic function of hematopoietic stem cells (c).
Figure 27:
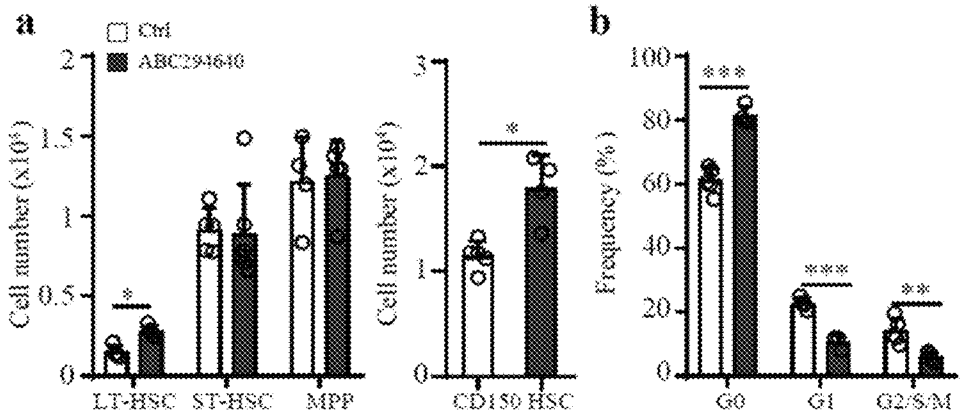
FIG. 27. illustrates the absolute number of HSPCs (LT-HSC, ST-HSC, MPP and CD150HSC) in the bone marrow (a) and cell cycle analysis of CD150 HSCs (b) in bone marrow from C57BL/6J mice after ABC294640 or solvent control treatment (n=5 mice). Data represent mean±s.d. Two-tailed Student's t-tests were used to assess statistical significance. *P<0.05, P<0.01, *P<0.001.

As shown in FIG. 14, the Sphk2 inhibitors significantly increased the number of hematopoietic stem cells (by 1.7-fold, see panel b in FIG. 14), and enhanced the hematopoietic function of hematopoietic stem cells. Sphk2 inhibitor treated hematopoietic stem cells also increased the hematopoietic reconstitution level (1.5-fold increased at 16 weeks after transplantation, see panel c in FIG. 14) and were able to generate multi-hematopoietic lineages (panel d in FIG. 14) in the recipients. Further, the mice receiving ABC294640 treatment exhibited an expanded HSC pool (2.1-fold increase for LT-HSCs and 1.7-fold increase for CD150 HSCs) and increased quiescence (FIG. 27) compared with control mice treated with the solvent control.

Figure 28:
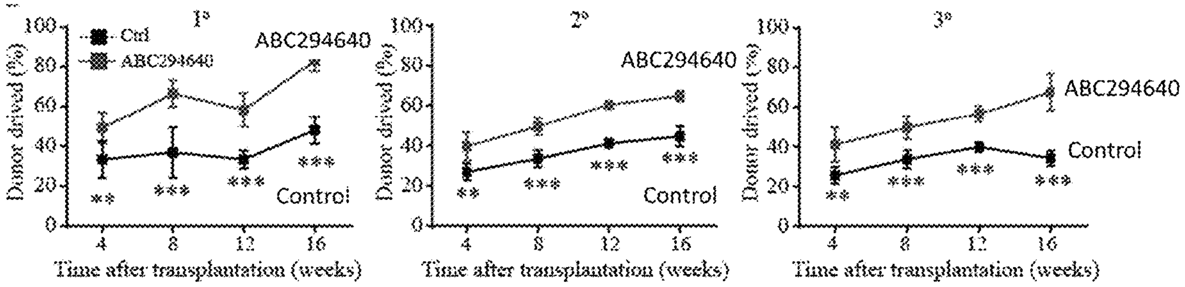
FIG. 28. illustrates the quantification of functional HSCs by transplantation assay. $2\times10^5$ bone marrow cells from C57BL/6J mice after 5FU and ABC294640 or vehicle control treatment were transplanted into irritated mice along with $2\times10^5$ recipient bone marrow cells. $1\times10^6$ bone marrow cells from primary or secondary recipient mice were transplanted into irritated mice in secondary or tertiary recipients respectively. PB analysis for total engrafted donor cells at the indicated number of weeks after transplantation.
Figure 29:
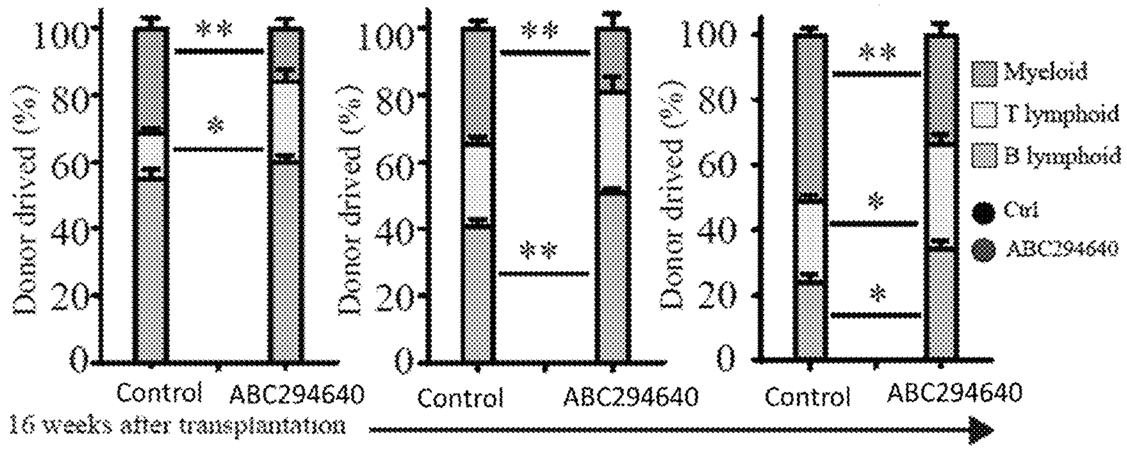
FIG. 29. illustrates the percentage of donor-derived B, T and myeloid lineage cells at 16 weeks after transplantation.
Figure 30:
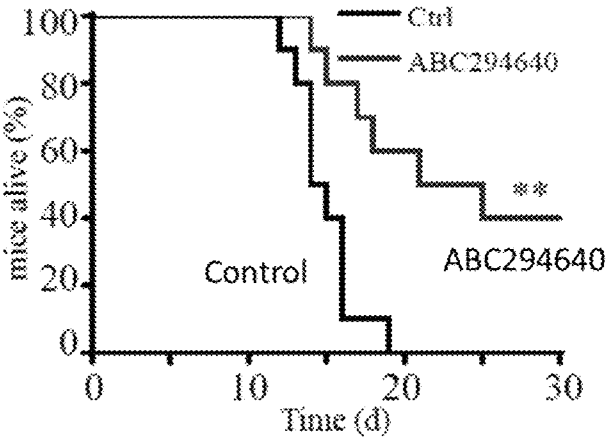
FIG. 30. illustrates the survival of C57BL/6J mice after serious 5FU treatment every 7 days and ABC294640 treatment every other day (n=10 mice group).

Repopulation analyses was also performed to investigate whether ABC294640 treatment functionally promotes HSC regeneration after chemotherapeutic stress. Mice receiving bone marrow cells after ABC294640 treatment gave significantly higher reconstitution through three rounds of 16-week observation period compared to mice received solvent control treated bone marrow cells (about 1.7-fold, about 1.5-fold and about 1.9-fold increase at 16 weeks in primary, secondary and tertiary transplantation respectively; FIG. 28). Consistently, the Sphk2 inhibitors also markedly promoted lymphopoiesis and suppressed myeloid skewing in recipients (FIG. 29). In agreement with the improved HSC regenerative potential, ABC294640 treated mice had notably increased survival after serial 5FU challenges compared to control (FIG. 30).

Example 15

Figure 31:
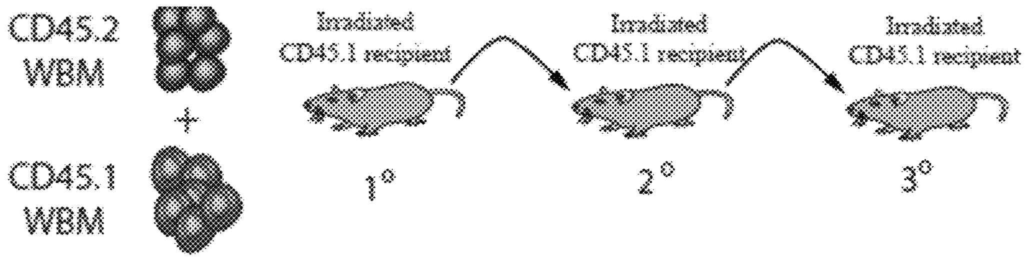
FIG. 31. illustrates the scheme for quantification of functional HSCs by transplantation assay. $2\times10^5$ bone marrow cells from Sphk1 knockout, Sphk2 knockout or control mice were transplanted into irritated mice along with $2\times10^5$ recipient bone marrow cells. $1\times10^6$ bone marrow cells from primary or secondary recipient mice were transplanted into irritated mice in secondary transplantation or tertiary transplantation respectively.
Figure 32:
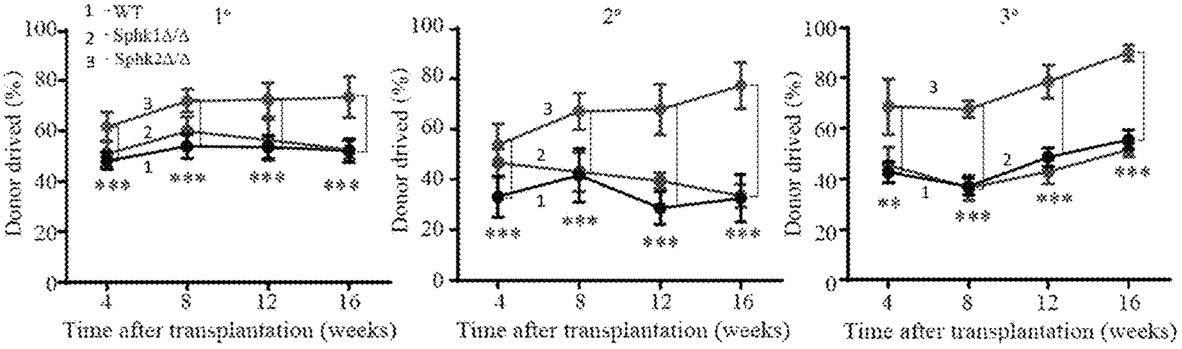
FIG. 32. illustrates the PB analysis for total engrafted donor cells at the indicated number of weeks after transplantation. The primary transplantation WT n=10 mice, Sphk1 knockout n=10 mice, Sphk2 knockout n=8 mice per group; secondary transplantation WT n=9 mice, Sphk1 knockout n=7 mice, Sphk2 knockout n=7 mice per group; tertiary transplantation WT n=7 mice, Sphk1 knockout n=8 mice, Sphk2 knockout n=6 mice per group.

To assess the long-term self-renewal potential of HSCs, $1\times10^6$ whole bone marrow cells from each recipient were serially transplanted into one irradiated mouse during each round of transplantation (FIG. 31). In primary, secondary and tertiary recipient mice, significantly higher levels of reconstitution from the Sphk2 but not Sphk1 deficient bone marrow cells than from control donor cells were observed (1.4-fold, 2.4-fold and 1.6-fold increase at 16 weeks in primary, secondary and tertiary transplantation, respectively) (FIG. 32).

Figure 33:
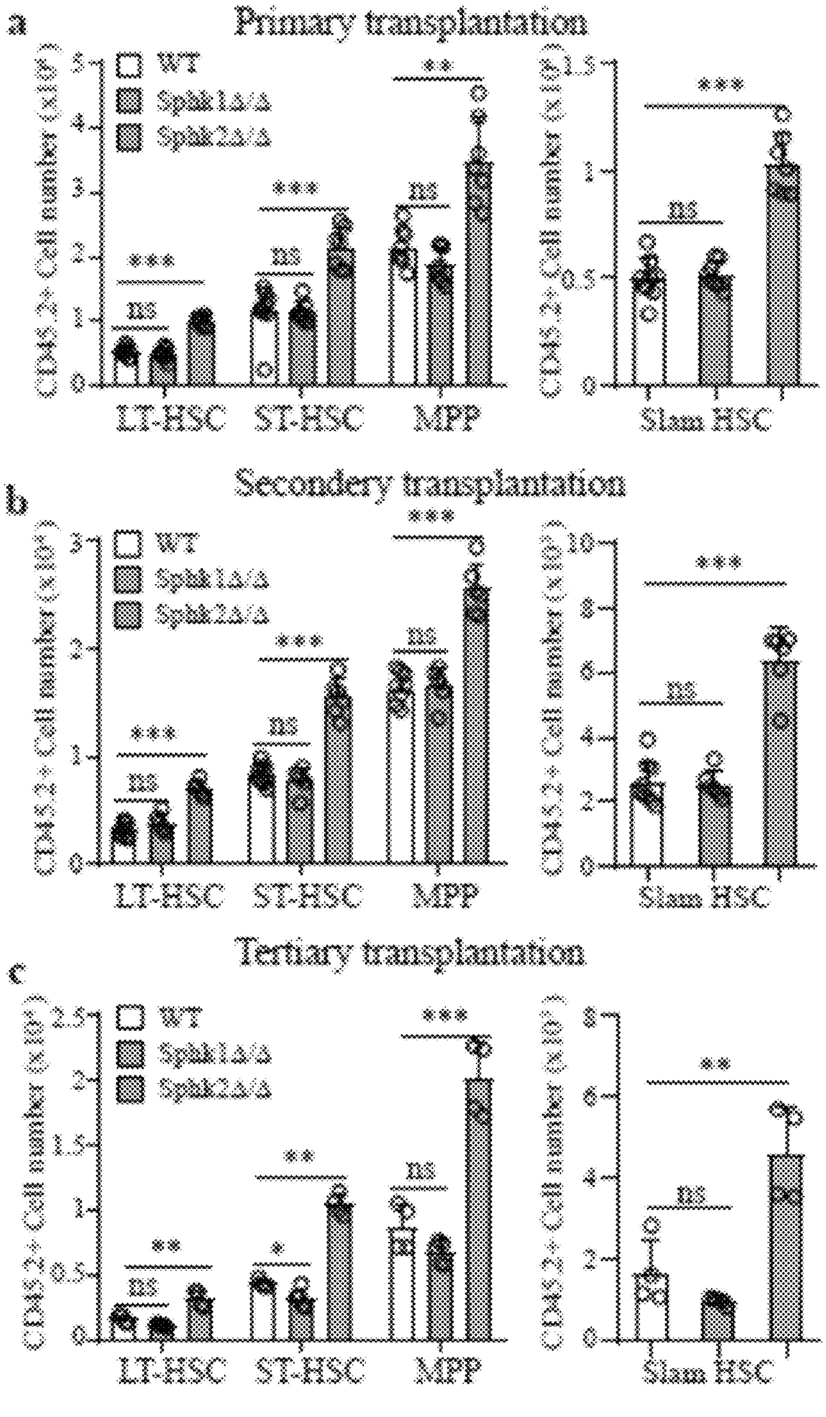
FIG. 33. illustrates the absolute numbers of donor derived HSPCs ($CD45.2^+$; LT-HSC, ST-HSC, MPP and CD150HSC) in the bone marrow were analyzed at 16 weeks after transplantation. Primary transplantation WT n=10 mice, Sphk1 knockout n=10 mice, Sphk2 knockout n=8 mice per group; secondary transplantation WT n=9 mice, Sphk1 knockout n=7 mice, Sphk2 knockout n=7 mice per group; tertiary transplantation WT n=7 mice, Sphk1 knockout n=8 mice, Sphk2 knockout n=6 mice per group). Data represent mean±s.d. Two-tailed Student's t-tests were used to assess statistical significance. *P<0.05, P<0.01, *P<0.001.
Figure 34:
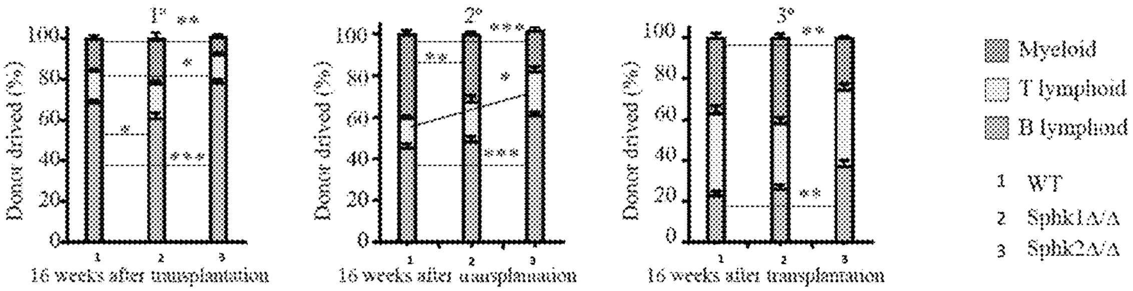
FIG. 34. illustrates the percentage of donor-derived B, T and myeloid lineage cells at 16 weeks after transplantation. The primary transplantation WT n=10 mice, Sphk1 knockout n=10 mice, Sphk2 knockout n=8 mice per group; secondary transplantation WT n=9 mice, Sphk1 knockout n=7 mice, Sphk2 knockout n=7 mice per group; tertiary transplantation WT n=7 mice, Sphk1 knockout n=8 mice, Sphk2 knockout n=6 mice per group.

Sphk2 deficient donor cells gave more donor derived HSPCs in recipients during 3 rounds of transplantation observations (FIG. 33). It was also observed that Sphk2 deficient bone marrow cells gave more lymphoid cells than myeloid cells during serious transplantations (FIG. 34).

All references as cited herein, including publications, patent applications and patents, are hereby incorporated by reference, as if it is individually and in particular stated that each of the references is incorporated by reference and to the extent that the reference is completely set forth herein.

In the context of the present application (especially in the context of the following claims, unless otherwise stated herein or clearly contradictory to the context, the terms "a" and "an" and "the" and "at least a/an/one" and similar referents are to be understood as comprising both singular and plural forms. Unless otherwise stated herein or clearly contradictory to the context, when the term "at least one" is followed by one or more of items as listed (for example, "at least one of A and B"), it is to be understood as one of the listed items (A or B) or any combination of two or more of the listed items (A and B). Unless otherwise noted, the terms "comprise," "have," "include," and "contain," are intended to mean an open term (i.e., meaning "including, but not limited to"). Unless otherwise defined in the context, recitation of ranges of values as used herein are merely intended to serve as a shorthand of a plural of each individual value falling within the range as individually listed, and each individual value is incorporated in the specification as if it is individually listed herein. Unless otherwise stated herein or clearly contradictory to the context, all the methods as described herein can be performed in any suitable order. Unless otherwise defined in the claims, any and all examples or exemplary languages (e.g., "such as") as used herein are merely intended to illustrative, and not to limit the scope of the application. Any language in the specification should not be construed as indicating that any element which is not claimed in the claims is necessary to practice the application.

Exemplifying embodiments of the present application are described herein, including the mode known by the inventors for carrying out the application. Upon reading of the description, variations of those exemplified embodiments will be apparent to those of ordinary skill in the art.

The inventors expect that the skilled person can apply such variants if required, and the inventors intend to implement the present application in a manner other than those specifically described herein. Thus, the present application includes all the modifications and equivalents of the subject matter described in the appended claims as permitted by applicable laws. Moreover, the present application comprises any combination of all possible variations of the aforesaid elements, unless otherwise indicated or clearly contradict with the context.

What is claimed:

1. A method for prolonging survival period of a subject suffering from chemotherapy-induced injury, comprising administering a therapeutically effective amount of Compound ABC294640 to the subject, wherein the chemotherapy-induced injury is caused by 5-fluorouracil, and the Compound ABC294640 has a structural formula of

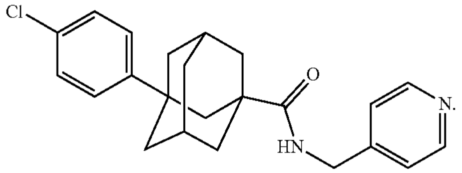

2. The method of claim 1, wherein said subject has been subjected to radiation.

3. The method of claim 1, wherein said subject has been subjected to bone marrow transplantation.

* * * * *